(12) United States Patent
Duraipandian et al.

(10) Patent No.: US 11,092,550 B2
(45) Date of Patent: Aug. 17, 2021

(54) METHOD FOR IDENTIFICATION OF LOW GRADE CERVICAL CYTOLOGY CASES LIKELY TO PROGRESS TO HIGH GRADE/CANCER

(71) Applicants: Technological University Dublin, Dublin (IE); The Provost, Fellows, Foundation Scholars, and the Other Members of the Board, of the College of the Holy and Undivided Trinity of Queen Elizabeth Near Dublin, Dublin (IE)

(72) Inventors: Shiyamala Duraipandian, Dublin (IE); Fiona Lyng, Dublin (IE); Damien Traynor, Dublin (IE); John O'Leary, Dublin (IE); Cara Martin, Dublin (IE); Padraig Kearney, Dublin (IE)

(73) Assignees: Technological University Dublin, Dublin (IE); The Provost, Fellows, Foundation Scholars, and the Other Members of Board, of the College of the Holy and Undivided Trinity of Queen Elizabeth Near Dublin, Dublin (IE)

( * ) Notice: Subject to any disclaimer, the term of this patent is extended or adjusted under 35 U.S.C. 154(b) by 68 days.

(21) Appl. No.: 16/472,337

(22) PCT Filed: Dec. 20, 2017

(86) PCT No.: PCT/EP2017/083753
§ 371 (c)(1),
(2) Date: Jun. 21, 2019

(87) PCT Pub. No.: WO2018/115088
PCT Pub. Date: Jun. 28, 2018

(65) Prior Publication Data
US 2020/0116638 A1    Apr. 16, 2020

(30) Foreign Application Priority Data

Dec. 21, 2016    (GB) ..................... 1621912

(51) Int. Cl.
*G01N 21/65*    (2006.01)
*G01J 3/44*    (2006.01)
(Continued)

(52) U.S. Cl.
CPC ............. *G01N 21/65* (2013.01); *G01J 3/44* (2013.01); *G01N 33/54373* (2013.01); *G01N 33/57411* (2013.01)

(58) Field of Classification Search
CPC ............ G01N 21/65; G01N 33/54373; G01N 33/57411; G01J 3/44
See application file for complete search history.

(56) References Cited

U.S. PATENT DOCUMENTS 7,396,970 B1    7/2008    Battiste
10,365,220 B2 *    7/2019    Chan ................... G01N 21/65
(Continued)

FOREIGN PATENT DOCUMENTS

EP    2984488 A1    2/2016
GB    2466442 A    6/2010
(Continued)

OTHER PUBLICATIONS

Nosheen R., et al., Raman microspectroscopy for the early detection of pre-malignant changes in cervical tissue, Experimental and Molecular Pathology, vol. 97, Issue 3, 2014, pp. 554-564, ISSN 0014-4800, https://doi.org/10.1016/j.yexmp.2014.10.013. (Year: 2014).*

(Continued)

*Primary Examiner* — Violeta A Prieto
(74) *Attorney, Agent, or Firm* — Winstead PC

(57) ABSTRACT

The present invention provides a method of using Raman spectroscopy for identification of low grade cervical cytol- (Continued)

ogy cases likely to progress to high grade/cancer. The Applicant has found that high quality Raman spectra can be successfully acquired from morphologically normal appearing cells from negative, LSIL and HSIL Thinprep® specimens and different grades of cervical pre-cancer can be separated with good sensitivities and specificities. Raman spectroscopy can further identify different categories of the LSIL cases i.e., whether they are likely to regress to negative or progress to HSIL cytology.

12 Claims, 19 Drawing Sheets

(51) Int. Cl.
*G01N 33/543* (2006.01)
*G01N 33/574* (2006.01)

(56) References Cited

U.S. PATENT DOCUMENTS

| | | |
|---|---|---|
| 2005/0277816 A1 | 12/2005 | Maier et al. |
| 2007/0167838 A1* | 7/2007 | Hubble ................ A61B 1/303 600/476 |
| 2010/0241357 A1* | 9/2010 | Chan .................... G01J 3/44 702/19 |
| 2011/0171628 A1 | 7/2011 | Meijer et al. |
| 2011/0317158 A1* | 12/2011 | Lyng .................... G01N 21/65 356/301 |
| 2014/0193805 A1 | 7/2014 | Patterson |
| 2014/0357509 A1 | 12/2014 | Ma et al. |
| 2016/0069809 A1* | 3/2016 | Bonnier ................ G01N 21/65 435/40.5 |
| 2017/0138860 A1* | 5/2017 | Huang .................. G01J 3/0218 |

FOREIGN PATENT DOCUMENTS

| | | |
|---|---|---|
| GB | 2514541 A | 12/2014 |
| WO | WO-2010003072 A1 | 1/2010 |
| WO | WO-2011072380 A1 | 6/2011 |

OTHER PUBLICATIONS

Jenkins, Gareth, "International Search Report," prepared for PCT/Ep2017/083753, dated Mar. 16, 2018, three pages.

Ho, C-M, et al., "Human Papillomaviral Load Changes in Low-Grade Squamous Intraepithelial Lesions of the Uterine Cervix," British Journal of Cancer, vol. 95, No. 10, Oct. 24, 2006, pp. 1384-1389.

Lyng, Fiona M., et al., "Raman Spectroscopy for Screening and Diagnosis of Cervical Cancer," Analytical and Bioanalytical Chemistry, vol. 407, No. 27, Aug. 16, 2015, pp. 8279-8289.

Duraipandian, Shiyamala, et al., "Near-Infrared Raman Spectroscopy for Assessing Biochemical Changes of Cervical Tissue Associated With Precarcinogenic Transformation," Analyst, vol. 139, No. 21, Jan. 1, 2014, pp. 5379-5386.

Ramos, I.R., et al., "Raman Spectroscopy for Cytopathology of Exfoliated Cervical Cells," Faraday Discussions, vol. 187, Jan. 1, 2016, pp. 187-198.

* cited by examiner

METHOD FOR IDENTIFICATION OF LOW GRADE CERVICAL CYTOLOGY CASES LIKELY TO PROGRESS TO HIGH GRADE/CANCER

FIELD

The present application relates to a method for identification of low grade cervical cytology cases likely to progress to high grade/cancer.

BACKGROUND OF THE INVENTION

1. Cervical Cancer

Cervical cancer is the fourth most common cancer in women worldwide, accounting for an estimated 528,000 new cases and 266,000 deaths in 2012. The mortality associated with cervical cancer can be reduced if this disease is detected at the early stages of development or at the pre-malignant stage (cervical intraepithelial neoplasia, CIN). Unlike most other types of cancer, cervical cancer affects mainly younger women, with about 60% of cases occurring in women under 50 years of age. Persistent infection with high risk human papillomavirus (HPV) (e.g., HPV types 16, 18) is accepted as the major cause for the development of cervical pre-cancer and cancer. Other risk factors include smoking, immunosuppression, long term use of oral contraceptives and socioeconomic status.

Cervical cancer begins in the basal layer of cells lining the cervix when the normal cells slowly change into pre-cancer cells that have the potential to turn into cancer. The gradual progression of cervical cancer can allow the detection of dysplastic changes before invasive cancer develops, through cervical cancer screening programmes. These screening programmes are common in developed countries, greatly reducing the mortality rates due to cervical cancer, but are not yet implemented in developing countries due to lack of infrastructure and funding.

2. Cervical Cancer Screening and Diagnosis 2.1 The Pap Test and HPV Testing

The Pap test, also called the Pap smear, cervical smear or smear test, is a screening method invented independently by Georgios Papanicolau and Aurel Babeş, but named after Papanicolau. It was introduced in the mid 1940s and currently it is the most common screening method for cervical neoplasia and its precursor lesions. The smear is collected by scraping the internal wall of the cervix with a cervical brush to obtain representative material from the transformation zone where the stratified squamous epithelium of the ectocervix turns into the columnar mucus secreting epithelium of the endocervix. The cells are then transferred onto a microscope slide by either the conventional method, in which the cells are spread along the slide immediately after collection and fixed with a spray fixative, or by liquid based cytology (LBC), in which the cells are transferred immediately after collection into a vial with a fixative solution and subsequently processed to remove debris and transferred to a slide (ThinPrep® (Hologic) or SurePath® (BD)). Once on a slide, the cells are Pap stained and evaluated under the microscope by a highly trained cytotechnologist or a pathologist according to the Bethesda system.

Cervical cytology is normally graded as negative (negative for intraepithelial lesion or malignancy [NILM]), low grade squamous intraepithelial lesion [LSIL] and high grade squamous intraepithelial lesion [HSIL]. LSIL may regress, but HSIL is unlikely to do so and may progress to invasive disease. Current cytology guidelines are that LSIL cases are re-tested after 6 months and HSIL cases are referred to colposcopy.

A normal Pap stained cervical pap smear typically shows cells from the surface of the epithelium, intermediate cells, which are large polygonal cells with a round to oval nucleus and a blue stained cytoplasm, and superficial cells, which are large polygonal cells with a small condensed nucleus and a pink to orange stained cytoplasm. Parabasal cells, which are small round or oval cells with the nucleus occupying half of the cell and a dense blue stained cytoplasm, can also be found, but these are more prominent in smears from postmenopausal women. Metaplastic cells, endocervical cells and endometrial cells can also all be present in a normal smear. The most common non-epithelial cells present in the normal smear are white blood cells, including polymorphs (neutrophils) or macrophages (histiocytes), which can increase in number due to infection and inflammation.

The advantages of the Pap test are that it is non-invasive, inexpensive and widely accepted. However, although it can have high specificity of up to 95-98%, sensitivity rates have been shown to vary from 74 to 96% due to sampling, technical and/or interobserver errors mainly associated with the subjectivity of the cytological screening [1].

Semi-automated screening systems consist of an automated microscope coupled to a workstation running image processing algorithms. Slides are scanned initially and cells of interest are separated from the background of inflammatory cells, cellular debris or overlapping cell clusters. Image segmentation algorithms perform a separation of the nuclei from the cytoplasm of the cells allowing the calculation of nuclear size, nucleus to cytoplasm ratio or even definition of the texture of the observed object. None of the currently available systems, however, FocalPoint® GS Imaging system (BD) or the ThinPrep® Imaging system (Hologic), provides fully automated screening without human intervention at some stage. The final decision still lies with the cytologist, resulting in the same subjectivity problem as in manual screening. The MAVARIC trial [1] showed no improvement in sensitivity or specificity of automated screening when compared to manual screening or in cost-effectiveness despite a 60%-80% increase in productivity for automated screening.

Most developed countries have screening programmes in place. For instance, CervicalCheck®—The National Cervical Screening Programme provides free cervical screening (smear tests) every 3-5 years to women aged 25 to 60 that are resident in the Republic of Ireland. CervicalCheck® recently commenced HPV triage—reflex HPV testing of smear test samples reported by cytology as showing a low grade abnormality [Low grade squamous intraepithelial lesions (LSIL) or Atypical Squamous Cells of Undetermined Significance (ASCUS)]. If the HPV test is negative, the recommendation will be routine re-call (3 or 5 years) reflecting the low risk of developing high-grade CIN in that interval. If the HPV test is positive, the recommendation will be refer to colposcopy. A biopsy will be taken to determine whether or not any disease (CIN) is present. When there is no CIN present, women will be discharged from colposcopy with a recommendation for a further smear test in 3 years, whatever their age.

Current technologies for cervical cancer screening are therefore cytology and HPV DNA testing. HPV mRNA testing and biomarker testing related to HPV mRNA are also being researched, but are not used routinely in screening. HPV DNA tests, such as Hybrid Capture 2 (Qiagen), Cervista HPV HR and Cervista HPV 16/18 (Hologic) and cobas HPV (Roche) assays, identify high-risk HPV oncogene expression, while HPV E6/E7 mRNA based assays, such as APTIMA HPV assay (Gen Probe), identify the messenger RNA of two HPV viral oncogenes, E6 and E7. However, these tests are expensive, time-consuming and provide no information on cervical cytopathology.

Over the last decade, prophylactic HPV vaccines have been developed, but, despite the introduction of these vaccines, there is still a need for regular cervical screening, as the vaccines do not protect against all oncogenic HPV types. Additionally, some women may not benefit from the vaccines if there is a pre-existing HPV infection or they do not receive the complete number of doses. After vaccination, women must still have routine Pap tests which can detect abnormal cervical growth regardless of what HPV type causes it to develop.

Currently there is an ongoing debate as to whether cytology (Pap tests) could be replaced by HPV DNA testing for primary cervical screening. HPV tests are recommended for women of any age with unclear Pap test results and for women over 30 years. HPV infection is very common in women under 30 years, but the HPV infection will clear in most young women within a few years and this will not lead to any adverse health effects. HPV is less common in women over 30 years and its presence may indicate a persistent infection over many years. This leads to an increased risk of cervical cancer in the future so these women need to be monitored more closely. With close monitoring for any pre-cancerous cells, early treatment can prevent cervical cancer before it has a chance to develop.

There remains a need for identifying and appropriately managing the treatment of women presenting with low grade cytological abnormalities. The proportion of women with low grade cytological abnormalities [Low grade squamous intraepithelial lesions (LSIL) or Atypical Squamous Cells of Undetermined Significance (ASCUS)] that will progress to develop a high grade lesion within a 24 month period is 21-28% for LSIL and 7.4% for ASCUS[i,ii]. This results in a large proportion of women with low grade cytological abnormalities who are at relatively low risk of developing cancer undergoing unnecessary colposcopic follow up and in many instances, treatment for cervical cancer when, in fact, such follow up and treatment may not be necessary. The UK TOMBOLA trial, estimated that more than 30% of women who underwent large loop excision (LLETZ) following a low-grade smear had been treated unnecessarily[iii]. There remains therefore considerable controversy over the most effective management of the large numbers of women presenting with low grade cytological abnormalities[iv,v], and it is likely that a combination of HPV testing and cytology screening will become a mandatory part of screening in these women.

2.2 Raman Spectroscopy

Raman spectroscopy is based on inelastic light scattering where the sample is illuminated by monochromatic laser light and interactions between the incident photons and molecules in the sample result in scattering of the light. The coupling of the light generates vibrations within the sample which are characteristic of the chemical structure. The energy of the scattered light is reduced by an amount equal to the vibrational energy. As a result, the positions, relative intensities and shapes of Raman bands carry in depth information about the molecular composition of the sample.

Cells and tissues contain a number of biochemical components such as DNA, RNA, proteins, lipids and carbohydrates and the Raman spectra of these samples are a superposition of the contributions from each individual biochemical component. It follows that Raman spectroscopy can provide a "biochemical fingerprint" of the cell or tissue. Additional analyses can be performed subsequently on the cell or tissue samples, such as staining, immunocytochemistry etc., as Raman spectroscopy can be performed in a label free, non-destructive manner. Over the past 15 years, Raman spectroscopy has been used for the diagnosis of a wide range of cancers, including breast, prostate, oesophageal, colon, lung, oral and cervical cancer, with excellent sensitivity and specificity values being reported [2, 3, 4].

Raman microspectroscopy has been used to distinguish between primary human keratinocytes (PHK), PHK cells expressing the E7 gene of HPV16 (PHK E7) and cervical cancer cells expressing HPV16 (CaSki). [5].

Ostrowska et al. [6] used both infrared absorption and Raman spectroscopy to study a range of cervical cancer cell lines. HPV negative (C33a) and low HPV copy number (SiHa with 1-2 copies) cell lines were shown to be biochemically similar, but significantly different from mid (HeLa) and high (CaSki) HPV copy number cervical cancer cell lines.

A study by Vargis et al. [7] used both cell lines and cytology samples to investigate the potential of Raman micro-spectroscopy to detect the presence of HPV.

Two further publications [8, 9] describe studies of cervical cytology samples using Infrared spectroscopy where HPV testing has been performed.

All of the publications to date use methods of testing for HPV DNA. No prior publication has been published which relates to using HPV mRNA status in order to improve discrimination of patients with LSIL to distinguish those patients who will go on to develop high grade lesions from those patients with LSIL who will not.

The following patent publications relate to methods to distinguish between transient or persistent HPV infection or to predict disease progression.

Title: DIFFERENTIATION BETWEEN TRANSIENT AND PERSISTENT HIGH-RISK HPV INFECTION BY IN SITU HYBRIDIZATION
Publication Number: US2014357509 (A1)
Publication Date: 2014 Dec. 4
Applicant(s): ADVANCED CELL DIAGNOSTICS [US] INC Title: HPV E6, E7 MRNA Assay and Methods of Use Thereof
Publication Number: US2014193805 (A1)
Publication Date: 2014 Dec. 10
Applicant(s): [US] INCELLDX INC Title: CERVICAL SCREENING ALGORITHMS
Publication Number: US2011171628 (A1)
Applicant(s): VERENIGING VOOR CHRISTELIJK [NL] HOGER ONDERWIJS WETENSCHAPPELIJK ONDERZOEK EN PATIENTENZORG Title: A HISTOCHEMICAL METHOD TO IDENTIFY AND PREDICT DISEASE PROGRESSION OF HUMAN PAPILLOMA VIRUS-INFECTED LESIONS
Publication Number: WO2010003072 (A1)
Applicant(s): STATEN ISLAND UNIVERSITY [US] HOSPI
[US] THE FEINSTEIN INST MEDICAL RES
[US] CASTELLANOS MARIO R However, the disclosed methods are based on histochemical staining or in situ hybridisation or other molecular biology methods and do not disclose the use of Raman spectroscopy in a method of distinguishing between transient HPV infection and persistent HPV infection, nor do the known methods use Raman spectroscopy to predict disease progression from low grade lesions to high grade lesions.

SUMMARY

According to the present invention, there is provided a method for distinguishing between low-grade squamous intraepithelial lesions (LSIL) that are likely to progress to high-grade squamous intraepithelial lesions (HSIL) and LSIL that are likely to regress to negative, the method comprising, consisting essentially of or consisting of the steps of:
providing a biological sample comprising cervical cells;
obtaining a Raman spectrum for the biological sample; and
analysing the Raman spectrum to determine whether the Raman spectrum falls within one or more predefined classes of cells, wherein the one or more predefined classes of cells comprise cells comprising LSIL that are likely to progress to HSIL and cells comprising LSIL that are likely to regress to negative.

The present invention provides a method of identifying and appropriately managing the treatment of women presenting with low grade cytological abnormalities, thus providing a cost-effective solution to distinguish between women with persistent low grade abnormalities at risk of disease progression and those likely to regress. The method of the present invention may be used to distinguish between transient and persistent HPV infection or to predict disease progression, in particular, to make a prognosis regarding the likelihood of low-grade squamous intraepithelial lesions (LSIL) progressing to high-grade squamous intraepithelial lesions (HSIL) or regressing to negative. An advantage of the present invention is that Raman spectroscopy alone may be used to provide a prognosis. This replaces the need to separately carry out cytology screening and test for the presence of HPV DNA and HPV mRNA. Thus, the present invention provides a method of using Raman spectroscopy for discriminating between LSIL cases likely to progress to HSIL or cancer and those likely to regress such that patients having low grade samples can avoid undergoing invasive colposcopy. This represents an important unmet clinical need as a high proportion of women with LSIL who are at a relatively low risk of developing cancer undergo unnecessary colposcopy follow up and in many instances also undergo unnecessary treatment.

Typically therefore the method does not include a separate step of cytology screening or screening for the presence of HPV DNA and/or HPV mRNA.

The step of analysing the Raman spectrum to determine whether the Raman spectrum falls within one or more predefined classes of cells may comprise using a classification model. A suitable classification model may be built using a database of reference Raman spectra. The reference Raman spectra may comprise Raman spectra for one or more predefined classes of cells. In particular, the reference Raman spectra may comprise Raman spectra for one, several or all of the following: (i) negative samples, (ii) biological samples comprising low-grade squamous intraepithelial lesions (LSIL) that are positive for HPV mRNA and positive for HPV DNA and therefore likely to progress to high-grade squamous intraepithelial lesions (HSIL); (iii) biological samples comprising LSIL that are negative for HPV mRNA and positive for HPV DNA and therefore unlikely to progress to HSIL and are likely to regress to negative; (iv) biological samples comprising LSIL that are negative for HPV mRNA and negative for HPV DNA and therefore unlikely to progress to HSIL and are likely to regress to negative; and (v) biological samples comprising HSIL. The database of reference Raman spectra may be compiled by obtaining Raman spectra for biological samples and subjecting biological samples to HPV DNA testing (e.g. Cobas) and HPV mRNA testing (e.g. APTIMA). Cells comprising LSIL that are likely to progress to HSIL are positive for HPV mRNA and positive for HPV DNA and cells comprising LSIL that are likely to regress to negative are negative for HPV mRNA and either positive or negative for HPV DNA. Specifically, the presence of HPV E6/E7 mRNA indicates an active transforming HPV infection suggesting that the LSIL cases are more likely to progress to HSIL.

Raman Spectroscopy and HPV signatures are thus used to give a spectral signature which can identify whether the HPV infection is transient (and therefore likely to revert to normal) or persistent/integrated (and therefore likely to progress to cancer). This avoids the need for further testing for low grade cytology samples in cases where the HPV infection is transient. High sensitivity and specificity was achieved for the classification of LSIL cases with either an episomal HPV infection (i.e. not integrated into the host cell DNA) or a transforming HPV infection (i.e. integrated into the host cell DNA). The inventors have therefore shown that Raman spectroscopy can distinguish between women with LSIL cytology who are at risk of disease progression and those who are likely to regress.

The classification model may comprise multivariate statistical analysis, such as Partial Least Squares Discriminant Analysis (PLS-DA), principal component analysis, linear discriminant analysis, support vector machines and random forest methods. As the visual difference between the Raman spectra may be very subtle, multivariate analysis, such as PLS-DA, may be used to determine the spectral differences.

The biological sample may be obtained during a smear test or a Pap smear. The biological sample or the Pap smear may be processed using a liquid-based cytology test or conventional cytology. The liquid-based cytology test may be ThinPrep® or SurePath®.

The biological sample may comprise morphologically normal looking cells. In that case, the Raman spectrum may be obtained for the morphologically normal looking cells. The inventors surprisingly found that Raman spectra from morphologically normal appearing cells from HSIL cases could be reliably discriminated from cells from normal cases. This is an important finding which means that it is not necessary to find the rare, abnormal-appearing HSIL cells on each abnormal slide in order to distinguish the case as abnormal. This is a major benefit as finding the rare abnormal cells on the unstained slide preparations is very difficult and time consuming.

The biological sample may comprise epithelial cells comprising basal, superficial and intermediate cells. The biological sample may comprise both superficial and intermediate epithelial cells as the morphologically normal looking cells. The present inventors have shown that the diagnostic efficacy of identifying HSIL is not affected by mixing morphologically normal appearing intermediate and superficial epithelial cell types. They have shown that either intermediate or superficial epithelial cells or both can be used to discriminate between negative and HSIL cytology cases. Superficial and intermediate cells are the most abundant cells on the Pap smear and they are very difficult to distinguish in the unstained slides so being able to use either cell type to classify normal versus abnormal smears is of major benefit.

The Raman spectrum may be obtained from cell nuclei of the cells from the biological sample. This provides more consistency in Raman spectra of superficial cells. Higher spectral variability due to variable glycogen content is seen if the Raman spectra are taken from the cytoplasm.

The Raman spectrum may be obtained using a low resolution Raman spectroscopy device, for example, having a spectral resolution worse than 3 wavenumbers.

The step of analysing the Raman spectrum may comprise analysing Raman peaks selected from one or more or all of the following: 482, 621, 728, 828, 855, 936, 957, 1092, 1176, 1210, 1338, 1422, 1450, 1578, 1610, 1619, 1669 cm$^{-1}$. These peaks are shown in FIG. 4 as being discriminating features for negative versus HSIL. The step of analysing the Raman spectrum may in addition or alternatively comprise analysing Raman peaks selected from one or more or all of the following: 785, 936, 1000, 1046, 1097, 1124, 1238, 1340, 1575 and 1652 cm$^{-1}$. These peaks are shown in FIG. 9(b) as being discriminating features related to HPV.

If it is determined that the Raman spectrum falls within a predefined class of cells comprising LSIL that are likely to progress to HSIL or cancer, the patient from whom the biological sample was obtained may undergo further investigation (e.g. colposcopy) and/or treatment. If it is determined that the Raman spectrum falls within a predefined class of cells comprising LSIL that are likely to regress to negative, the patient from whom the biological sample was obtained may be retested after a period of years, for example, 3 years.

BRIEF DESCRIPTION OF THE DRAWINGS

The present application will now be described with reference to the accompanying drawings in which.

DETAILED DESCRIPTION

The words comprises/comprising when used in this specification are to specify the presence of stated features, integers, steps or components, but do not preclude the presence or addition of one or more other features, integers, steps, components or groups thereof. In certain embodiments, the term comprises or comprising may be understood to mean includes or including, i.e. other components are also present. In alternative embodiments, the term comprises or comprising may be understood to mean consists of or consisting of, i.e. no other components are present.

Typically the terms "subject" and "patient" are used interchangeably herein. The subject is typically a mammal, more typically a human.

Figure 1:
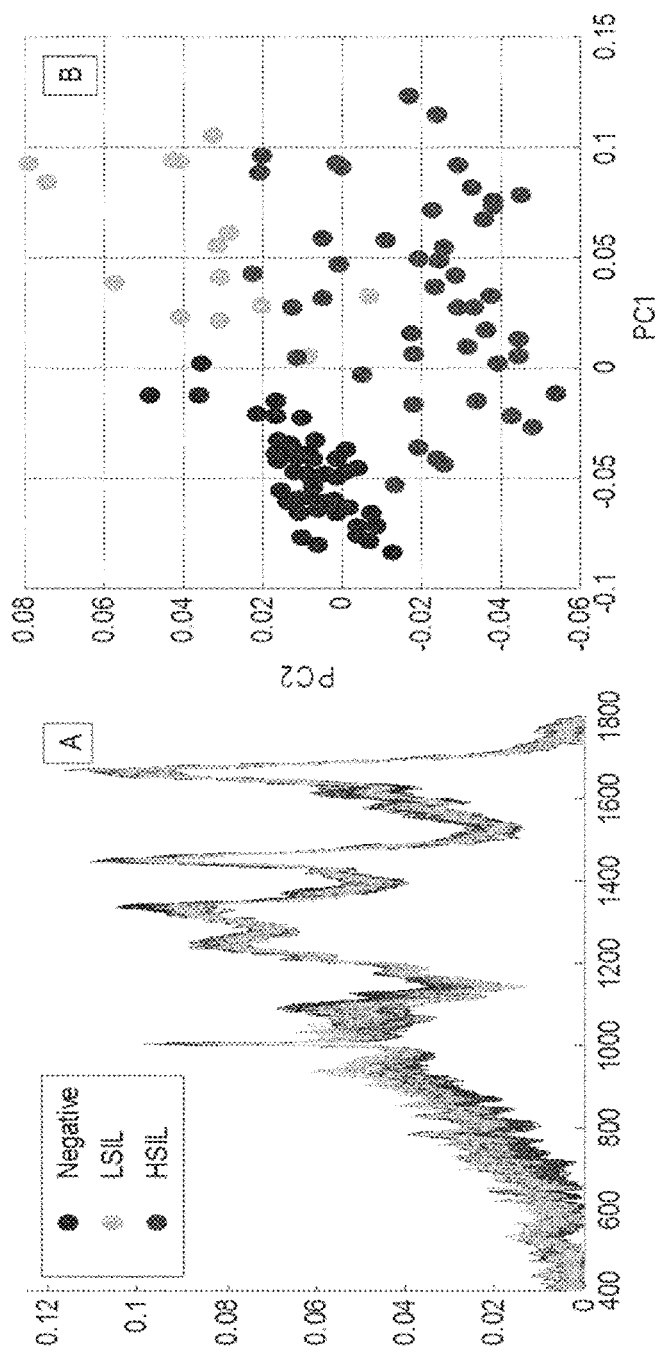
FIG. 1 shows (A) Raman spectra and (B) Principal Components Analysis scores plot showing good discrimination between normal (black), LSIL (light grey) and HSIL (dark grey) cells.

The present invention provides a system and method using Raman spectroscopy for accurately discriminating between normal (NAD), LSIL and HSIL Thinprep® cytology samples. Specifically, a system and method using Raman spectroscopy to successfully discriminate between the spectra of normal cells (blue), and abnormal cells, LSIL (green) and HSIL (red) (FIG. 1) are provided. The Inventors surprisingly found that Raman spectra from morphologically normal appearing cells from HSIL cases could be reliably discriminated from cells from normal cases. This was an important finding which meant that it was not necessary to find the rare, abnormal-appearing HSIL cells on each abnormal slide in order to distinguish the case as abnormal. This proved to be a major benefit as finding the rare abnormal cells on the unstained slide preparations was very difficult and time consuming.

The following Examples describe the invention.

Example 1

Use of Superficial or Intermediate Epithelial Cells for Discrimination of Negative and HSIL Cytology Cases Materials and Methods
Sample Collection and Processing True negative cervical liquid based cytology samples were obtained from the cytology laboratory, Coombe Women and Infants University Hospital (CWIUH), Dublin, Ireland. HSIL cytology specimens were collected during the routine Pap smear from the Colposcopy clinic, CWIUH, Dublin, Ireland. The collected smears were processed via the ThinPrep® method. This study was approved by the Research Ethics Committee CWIUH. The cells were collected from the cervix using a cyto brush and then rinsed in the specimen vial containing PreservCyt transport medium (ThinPrep® Pap Test; Cytyc Corporation, Boxborough, Mass.). The labelled ThinPrep® sample vial was sent to the cytology laboratory equipped with a ThinPrep® processor. All samples were prepared using a ThinPrep® 2000 processor (Hologic Inc., Marlborough, Mass. 01752). The Thin-Prep® processor homogenizes the sample by spinning either the filter (T2000) or the vial (T3000), creating shear forces in the fluid that are strong enough to disaggregate randomly joined material, break up blood, mucus and non-diagnostic debris while keeping true cell clusters intact. The cells were then collected onto the membrane of the TransCyt filter and further transferred onto a glass slide to create a monolayer deposit of cells (~20 mm in diameter). The slide was transferred into a fixative bath of 95% ethanol automatically. In total, 32 unstained cytology samples on ThinPrep® slides (17 negative and 15 HSIL) were obtained and subjected to Raman spectroscopic analysis. Before Raman measurement, each slide was pre-treated with hydrogen peroxidase ($H_2O_2$) to remove any contaminating blood and debris.

Raman Instrumentation

Raman spectra were recorded using a HORIBA Jobin Yvon XploRA® system (Villeneuve d'Ascq, France), incorporating an Olympus microscope BX41 equipped with a ×100 objective (MPlanN, Olympus, NA=0.9). The system consists of a 532 nm diode laser, 1200 lines/mm grating and an air-cooled CCD detector (Andor, 1024×256 pixels). The system was wavelength calibrated to the 520.7 $cm^{-1}$ spectral line of silicon and also intensity-calibrated using a relative intensity correction standard (NIST 2242). A total of ~770 Raman signals were measured from the ThinPrep® specimens of 32 patients (17 negative and 15 HSIL). From each slide, 15 to 20 intermediate and superficial epithelial cells were randomly selected and good quality Raman spectra were obtained with an integration time of 30 sec and 2 accumulations to improve the signal to noise ratio. The laser power on the sample was ~1 mW. The image of the Raman measured cells were recorded and x- and y-coordinates of the measured cells were also stored. After the Raman spectral acquisition, the samples were Pap stained and each recorded cells was re-visited using the stored x- and y-coordinates to verify whether the cells were from the intermediate layer or superficial layer.

Data Analysis

All the recorded Raman spectra were corrected for the glass background using a linear least-squares method with non-negative constraints (NNLS). The least-squares model was developed using the basis spectra obtained from the pure glass slides and selected pure biochemicals (e.g., actin, collagen, RNA, DNA, etc.) that approximate the biochemical composition of cervical cells. The Raman dataset has also been corrected for the baseline and then vector normalized. The Raman data was mean-centered and then subjected to partial least squares discriminant analysis (PLS-DA) diagnostic algorithm together with leave-one-out, cross-validation for discriminating negative cytology and HSIL cytology. PLS-DA establishes a regression model between the Raman spectral dataset and the class membership. The class membership is a dummy dichotomous variable, coded with 0s and 1s to represent each observation. PLS-DA rotates the latent variables to obtain maximum separation among the classes. The analysis was performed using the PLS toolbox (Eigenvector Research, Wenatchee, Wash.) in the Matlab® (Mathworks Inc., Natick, Mass.) scripting environment.

Results

Figure 2:
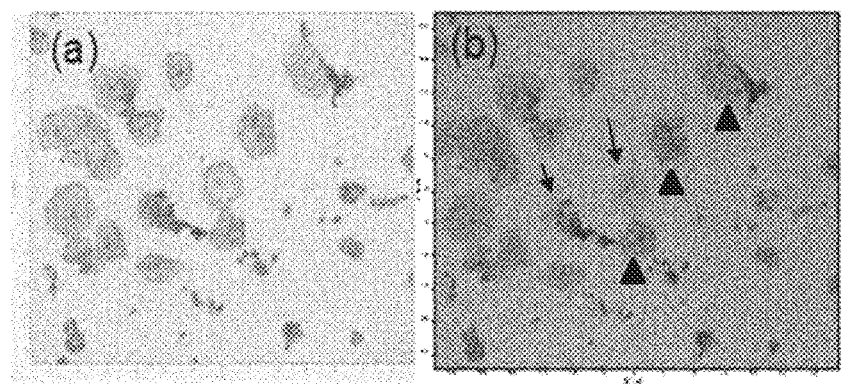
FIG. 2(a) is an unstained image ×10 and (b) Pap stained image ×10 of negative cytology specimen; in the Pap stained image (b) superficial cells stained orange to pink in color (indicated by arrows), and intermediate cells stained turquoise green to blue in color (indicated by arrowheads)
Figure 3A:
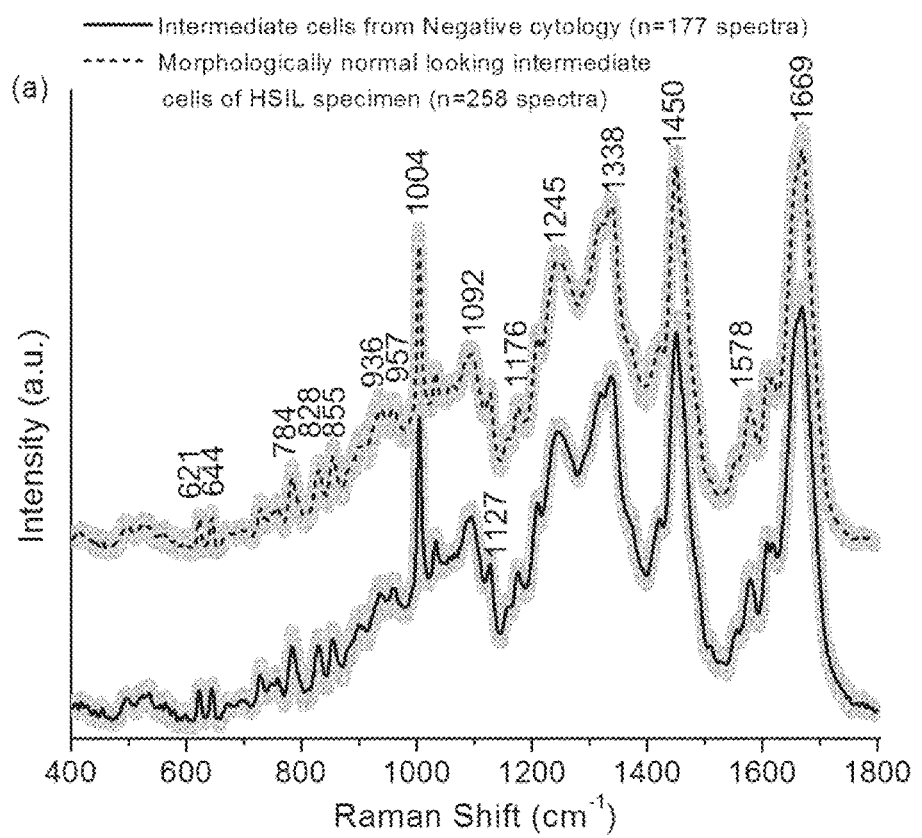
FIG. 3(a) shows the Mean Raman spectra±1 standard deviation (SD) acquired from the intermediate cells of negative cytology ThinPrep® specimen (n=17) and morphologically normal looking intermediate cells of high-grade squamous intraepithelial lesion (HSIL) ThinPrep® specimens (n=15) collected during routine Pap smear, (b) Mean Raman spectra±1 SD acquired from the superficial cells of negative cytology specimen (n=17) and morphologically normal looking superficial cells of HSIL cytology ThinPrep® specimens (n=12) collected during routine Pap smear.
Figure 3B:
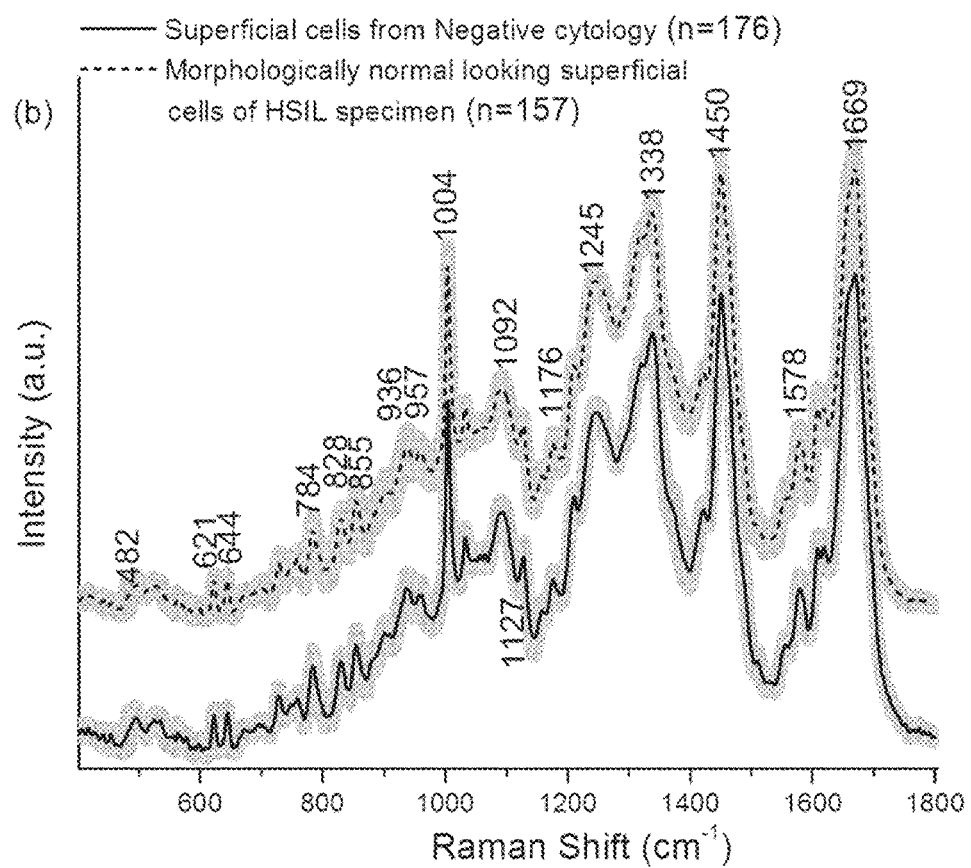
Figure 4:
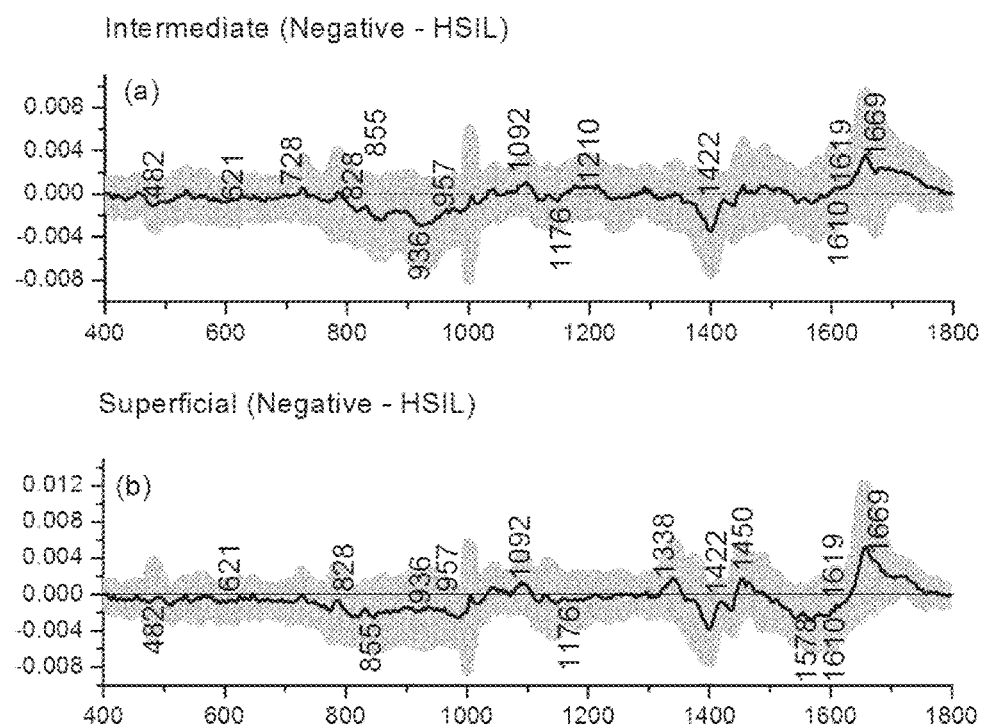
FIG. 4 shows the different Raman spectra±1 standard deviation (SD) obtained from (a) intermediate cells of negative and high-grade squamous intraepithelial lesion (HSIL) specimen (b) superficial cells of negative and HSIL specimen. It has to be noted that in the HSIL specimen Raman spectra were acquired from morphologically normal looking intermediate and superficial cells.

In this study, Raman spectra were acquired from the nuclei of 15 to 20 randomly selected cells from each ThinPrep® cervical cytology specimen. Here, Raman spectra were measured from the intermediate and superficial cells of negative cytology specimens and from morphologically normal appearing intermediate and superficial cells of HSIL cytology specimens. FIG. 2 shows the intermediate and the superficial cells collected from the negative cytology specimen. The intermediate and the superficial cells are indistinguishable in unstained slides ((FIG. 2(*a*)). After the Pap staining, the superficial cells are orange to pink in color, and the intermediate cells are turquoise green to blue in color (FIG. 2(*b*)). Raman spectra were recorded from the unstained slides. The mean normalized Raman spectra obtained from the intermediate (negative (n=177), HSIL (n=258), FIG. 3*a*) and the superficial (negative (n=176), HSIL (n=157) FIG. 3*b*) cells are shown in FIG. 3. The Raman spectra obtained from the intermediate (maximum standard deviation (SD)=±0.0049) and superficial (maximum SD=±0.0056) cells are quite consistent. However larger spectral variability have been reported for the superficial layer due to the variation in the glycogen content associated with women's age, hormonal levels and menstrual cycle. The consistency observed in our Raman spectra of superficial cells is because the Raman signals were measured from the cell nucleus; whereas high spectral variability due to the glycogen content is seen if the Raman spectra are taken from the cytoplasm. The measured Raman spectrum contains complex, overlapped spectral signatures in relation to the tissue biochemistry. Weak Raman peaks can be observed at 482 $cm^{-1}$ (glycogen), 621 and 644 $cm^{-1}$ (proteins), 728 and 784 $cm^{-1}$ (DNA), and 828 $cm^{-1}$ (DNA/RNA). More prominent peaks are visible in the vicinity of 855 and 936 $cm^{-1}$ (glycogen and proteins), 957 $cm^{-1}$ (DNA), 1004 $cm^{-1}$ (phenylalanine), 1035 $cm^{-1}$ (proteins), 1092 $cm^{-1}$ (DNA phosphate backbone), 1127 $cm^{-1}$ (proteins), 1176 $cm^{-1}$ (cytosine/guanine), 1210 $cm^{-1}$ (tryptophan and phenylalanine), 1245 $cm^{-1}$ (amide III), 1320 $cm^{-1}$ (DNA/RNA, proteins, amide III), 1338 $cm^{-1}$ (proteins and nucleic acids), 1422 $cm^{-1}$ (related to the DNA/RNA content), 1450 $cm^{-1}$ (proteins, lipids), 1578 $cm^{-1}$ (nucleic acids), 1610 $cm^{-1}$ (phenylalanine, tyrosine), 1619 $cm^{-1}$ (heme), and 1669 cm$^{-1}$ (amide I). The main Raman peaks and their tentative assignments are summarized in Table 1. Visually, the Raman spectra obtained from the negative cytology specimens are dominated by protein bands (e.g., 1669 cm$^{-1}$). DNA and nucleic acids (1422 and 1578 cm$^{-1}$), heme and other proteins (1610 and 1619 cm$^{-1}$) are higher in abnormal samples. The main differences between the Raman spectra acquired from the intermediate (FIG. 4a) or superficial (FIG. 4b) cells from the negative and HSIL cytology specimens were observed at 482, 621, 728, 828, 855, 936, 957, 1092, 1176, 1422, 1450, 1578, 1610, 1619, and 1669 cm$^{-1}$ (unpaired two-sided Student's t-test, p<0.001). These bands are mainly related to DNA, proteins and glycogen. This can be explained from the fact that the intermediate layer is the transitional layer between the immature cells from the basal/parabasal layer and the mature cells of the superficial layer. Hence, both of the cell layers (i.e., intermediate and superficial layers) may have similar molecular composition such as glycogen, DNA, proteins and lipids. The intermediate cells also showed significant changes at 1210 cm$^{-1}$ corresponding to proteins (FIG. 4(a)). Similarly, the superficial cells also indicated prominent changes for proteins and nucleic acids (1338 cm$^{-1}$, FIG. 4(b)). When the spectra of both cell types were mixed, the spectral changes were observed around the Raman peaks 482, 621, 828, 855, 936, 957, 1092, 1210, 1338, 1422, 1450, 1578, and 1669 cm$^{-1}$ (FIG. 4). In short, both of the cell types yielded similar diagnostic information associated with HSIL.

Figure 5A:
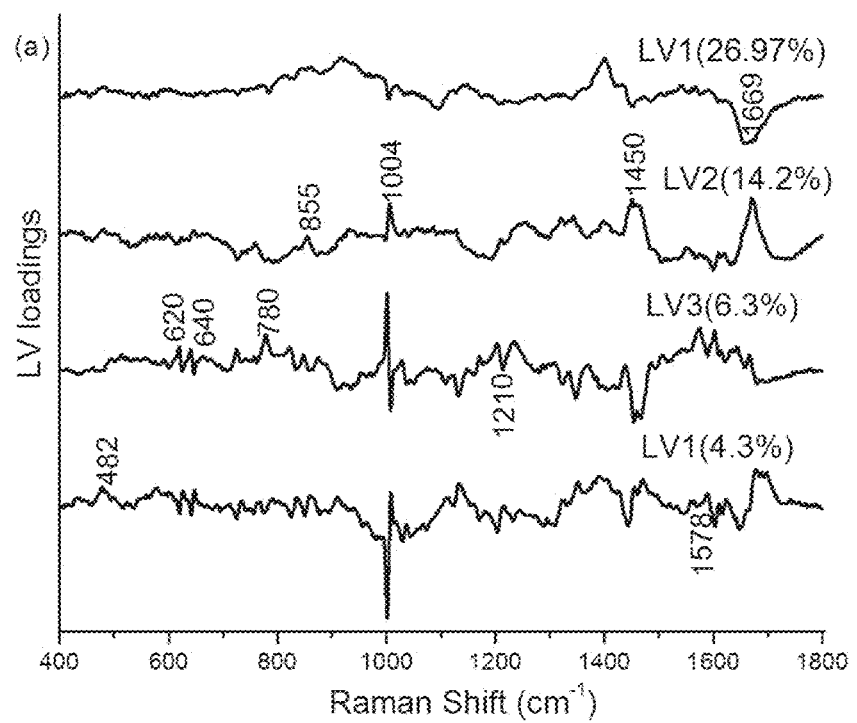
FIG. 5 shows PLS loadings (LVs) of the developed PLS-DA model for the dataset obtained from (a) intermediate cells, (b) superficial cells and (c) mixed intermediate and superficial cells. (Latent variables (LVs), partial least squares discriminant analysis (PLS-DA))
Figure 5B:
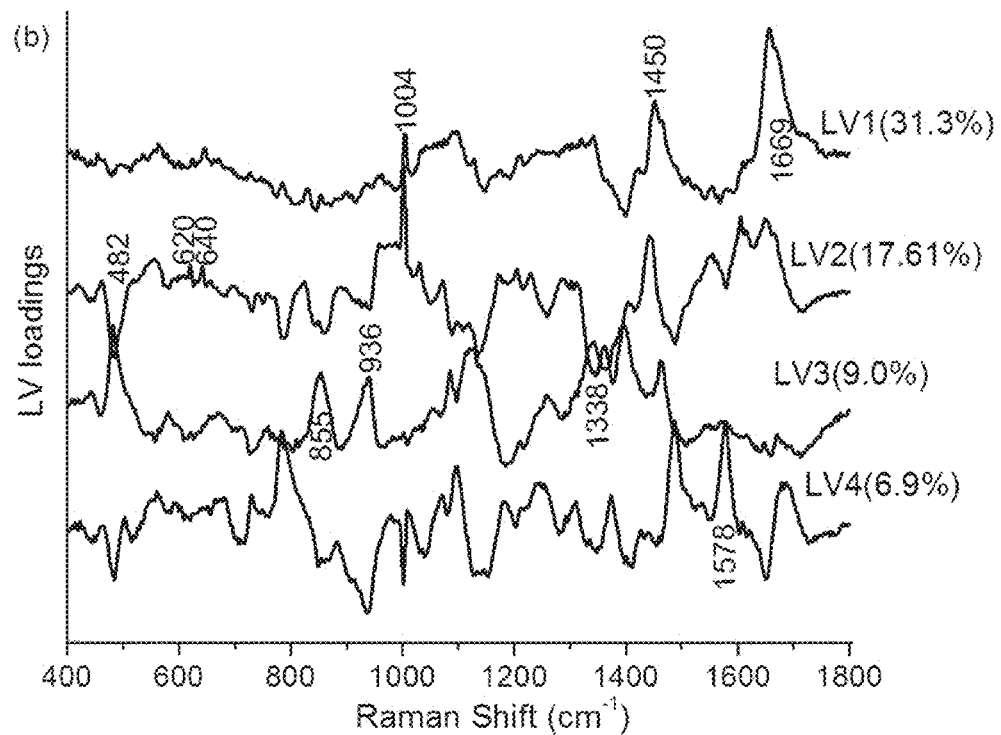
Figure 5C:
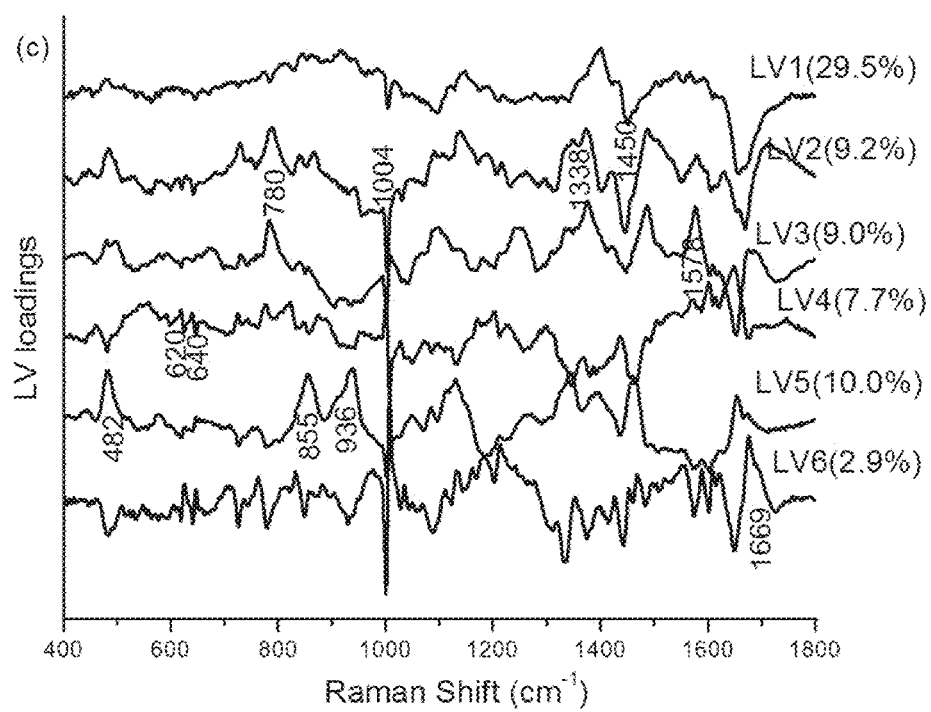
Figure 6:
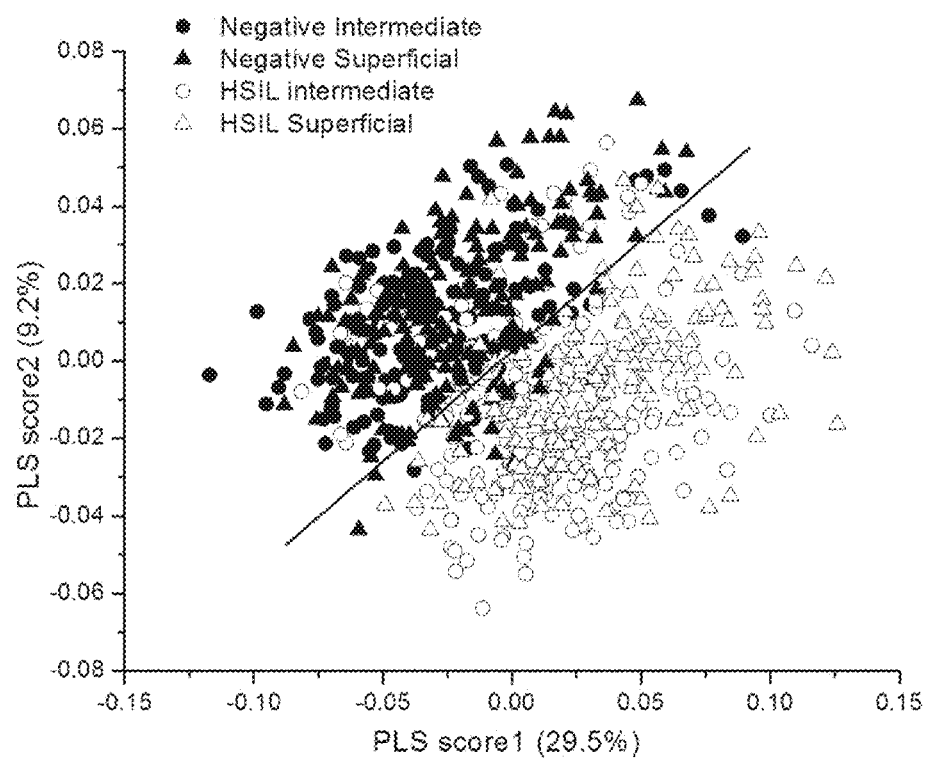
FIG. 6 Scatter plot of the significant latent variables (LVs) obtained from the Raman spectral dataset of mixed intermediate and superficial cells of negative and high-grade squamous intraepithelial lesion (HSIL) cytology specimen.
Figure 7A:
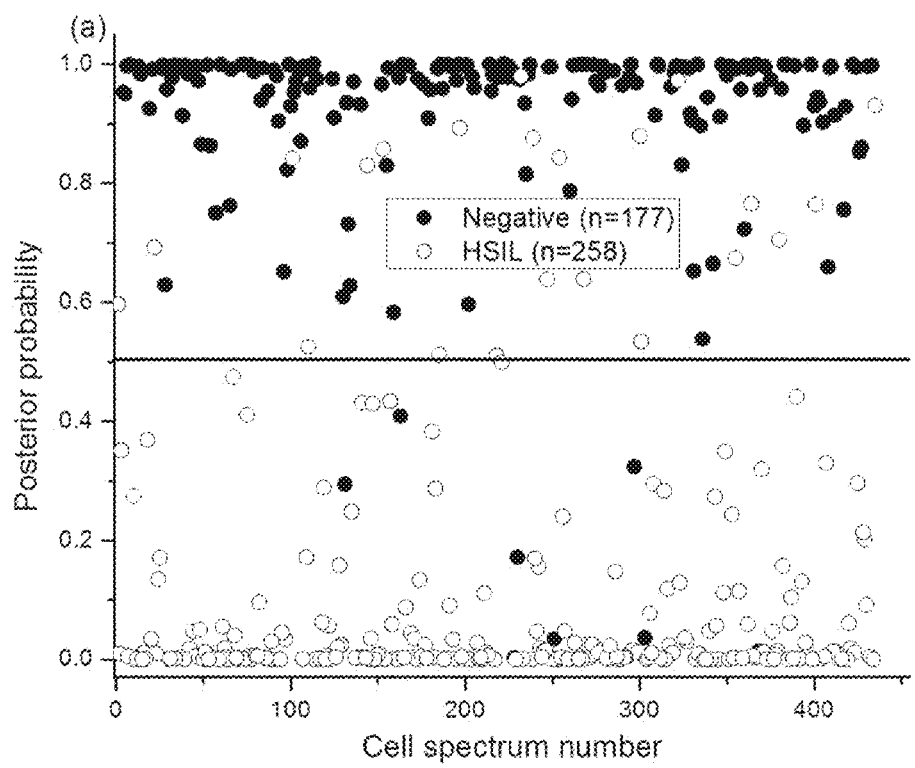
FIG. 7 is a scatter plot of the posterior probability values calculated from the Raman dataset obtained from (a) intermediate cells, (b) superficial cells and (c) mixed intermediate and superficial cells of negative and HSIL cytology specimens.
Figure 7B:
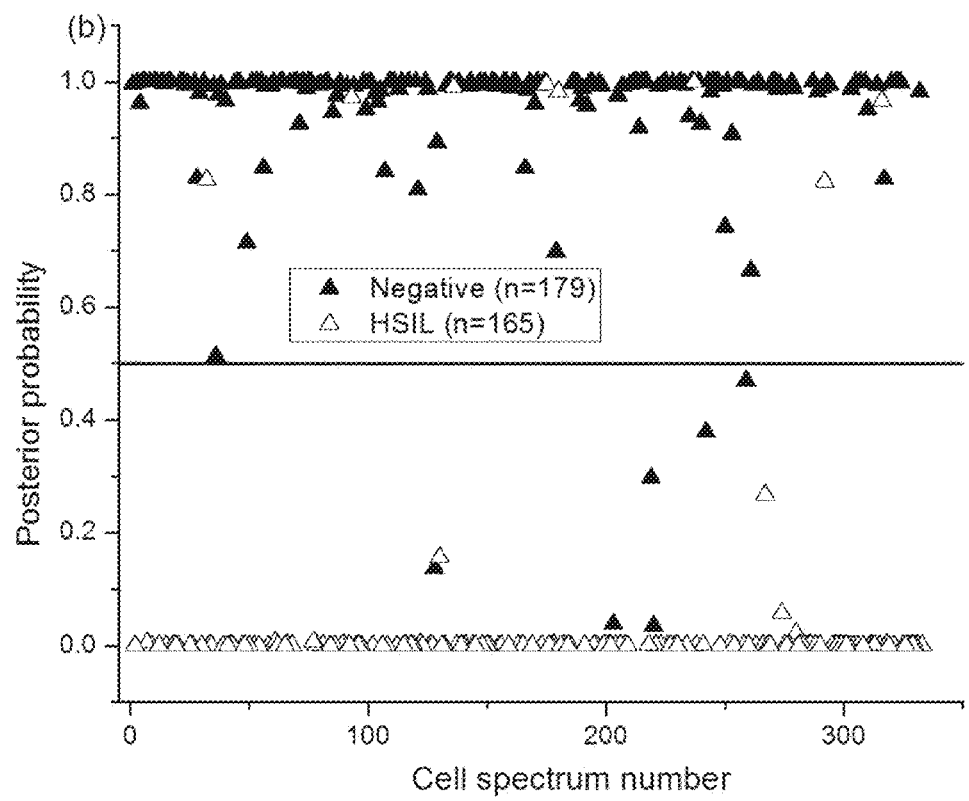
Figure 7C:
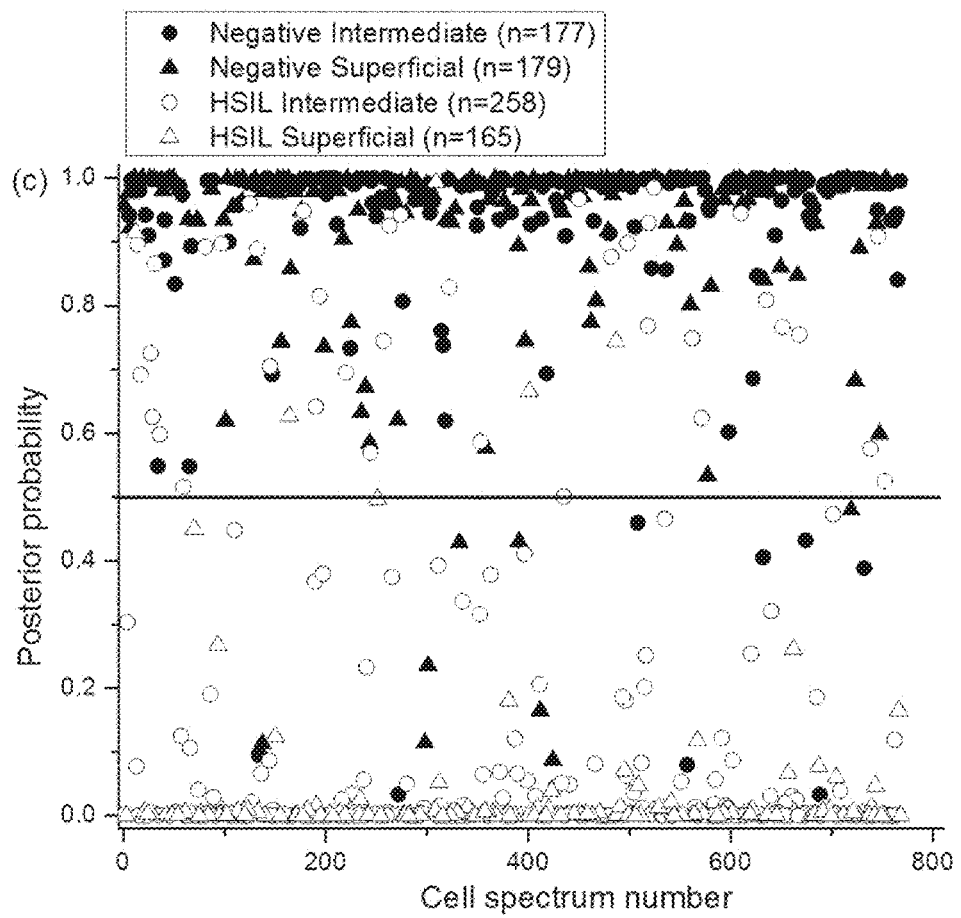

As the visual difference between the Raman spectra from the negative and HSIL cytology specimens are however very subtle, multivariate analysis, PLS-DA, was utilized to enhance the spectral differences. Leave-one-out, cross-validated PLS-DA models were developed from the dataset collected from the intermediate cells and the superficial cells from negative and HSIL cytology specimens. The PLS-DA model was also developed for the mixed intermediate/superficial dataset. The number of components (4 LVs, 4 LVs and 6 LVs, FIG. 5) corresponding to the minimum cross-validation error were utilized to develop the models for the intermediate, superficial and mixed intermediate/superficial datasets, respectively. The LVs for the superficial dataset accounted for 64.78% and 81.48% of the total Raman spectral variations in the X and Y directions and predominantly provided information about DNA and proteins (620, 640, 1004, 1338, 1450, and 1578 cm$^{-1}$), glycogen and proteins (482, 855, 936, and 1655 cm$^{-1}$). Similarly, the LVs (51.72% and 71.19% variations in X and Y direction) corresponding to the intermediate dataset mainly showed the changes in glycogen, DNA and protein features (482, 620, 640, 780, 855, 1004, 1450, 1578, and 1669 cm$^{-1}$). Combining the intermediate and superficial dataset, the LVs (68.23% and 75.57% variations in X and Y direction) extracted the information around the Raman peaks such as 780, and 1578 cm$^{-1}$ (DNA), and 482, 620, 640, 855, 936, 1004, 1338, 1450, and 1669 cm$^{-1}$ (glycogen and proteins). From the above results, it is clear that both of the cells types either utilized separately or in combination provide almost the same diagnostic information for HSIL identification. The LV scores scatter plot (FIG. 6) obtained from the mixed intermediate/superficial dataset visually shows that the scores for the negative cytology specimens of intermediate and superficial cells are overlapped due to minimal variability. Similarly, the scores for the HSIL cytology specimens of intermediate and superficial cells are overlapped. However, the scores of both intermediate and superficial cells showed clear separation between the negative and HSIL cytology specimens. This reinforces the observation that the changes between the negative and HSIL cytology specimens is highly significant compared to the differences between the two cell types. However, some of the LV scores of the HSIL intermediate dataset are skewed towards the scores of the negative cytology specimens (FIG. 6). This can be attributed to the fact that some of the HSIL cytology specimens can regress back to normal or some of the cells in the HSIL specimen are still normal. The posterior probability plots from the developed PLS-DA models provided sensitivities of 91.5%, 94.9% and 93.0% and specificities of 95.5%, 96.6%, and 95.8% (Table 2) for identifying the HSIL cases based on the spectral dataset obtained from the intermediate (FIG. 7a), superficial (FIG. 7b), and mixed intermediate/superficial cells (FIG. 7c). The posterior probability plot of mixed intermediate/superficial cells (FIG. 7c) further shows that the diagnostic efficacy of identifying HSIL is not affected by mixing the intermediate and superficial cell types. This shows that either intermediate or superficial epithelial cells or both can be used to discriminate between negative and HSIL cytology cases. Superficial and intermediate cells are the most abundant cells on the Pap smear and they are very difficult to distinguish in the unstained slides so being able to use either cell type to classify normal vs. abnormal smears is of major benefit.

TABLE 1

Main Raman peaks

| Wavenumber (cm$^{-1}$) | Raman Peak Assignments |
|---|---|
| 482 | Glycogen |
| 621 | C—C twisting mode of Phenylalanine (proteins) |
| 644 | C—C twisting mode of Tyrosine and Phenylalanine |
| 728 | C—N stretching in Adenine and lipids |
| 784 | Uracil, Thymine, Cytosine (ring breathing modes in the DNA/RNA) |
| 828 | PO$_2$ stretching in DNA, Tyrosine |
| 855 | Ring breathing in Tyrosine and Proline (proteins) |
| 936 | C—C stretching mode of Proline and Valine |
| 957 | C—C and C—N stretch PO$_3^{2-}$ stretch (DNA) |
| 1004 | C—C aromatic ring stretching in Phenylalanine |
| 1035 | C—H bending mode in Phenylalanine, C—N stretching in proteins |
| 1092 | Symmetric PO$_2^-$ stretching vibration of the DNA |
| 1127 | C—N stretching in proteins |
| 1176 | C—H in plane bending mode of Tryptophan & Phenylalanine; Cytosine, Guanine |
| 1210 | C—C$_6$H$_5$ stretching mode in Tryptophan & Phenylalanine |
| 1245 | Amide III (of collagen) |
| 1320 | Guanine (ring breathing modes of the DNA/RNA bases) - C—H deformation (protein); Amide III (α-helix) |
| 1338 | CH$_2$/CH$_3$ wagging & twisting mode in collagen, nucleic acid & tryptophan |
| 1422 | CH$_3$ asymmetric stretch (lipids, aromatics) |
| 1450 | CH (CH$_2$) bending mode in proteins and lipids |
| 1578 | Adenine, Guanine (DNA/RNA); C=C bending mode of Phenylalanine |
| 1610 | C=C Phenylalanine, Tyrosine and Tryptophan |
| 1619 | C=C Phenylalanine, Tyrosine and Tryptophan |
| 1669 | Amide I (C=O stretching, C—N stretching and N—H bending, proteins) |

TABLE 2

Calculated accuracy, sensitivity and specificity for differentiating negative and high-grade squamous intraepithelial lesion (HSIL) cytology using the Raman spectral dataset obtained from (i) intermediate cells, (ii) superficial cells and (iii) intermediate + superficial cells

| Type of cells | Sensitivity (%) | Specificity (%) | Accuracy (%) |
|---|---|---|---|
| Intermediate | 91.5 (236/258) | 95.5 (169/177) | 93.1 (405/435) |
| Superficial | 94.9 (149/157) | 96.6 (170/176) | 95.8 (319/333) |
| Intermediate + Superficial | 93.0 (386/415) | 95.8 (338/353) | 94.3 (724/768) |

This method was also used to classify negative, LSIL and HSIL cases. Table 3 shows sensitivity of 89.2%, 63.2% and 81.4% and specificity of 85.3%, 89.0% and 91.4% for identifying negative, LSIL and HSIL (Table 3). Negative and HSIL samples could be classified very well, but LSIL samples were more difficult to classify correctly. Some LSIL cases classified as normal while some classified as HSIL.

TABLE 3

Sensitivity and specificity for identifying negative, LSIL and HSIL samples

|  | TN (True Negative) | LSIL | HSIL |
|---|---|---|---|
| TN | 149 | 11 | 7 |
| LSIL | 50 | 129 | 25 |
| HSIL | 6 | 27 | 144 |
| Sensitivity | 89.2 | 63.2 | 81.4 |
| Specificity | 85.3 | 89.0 | 91.4 |

The following example explains this mis-classification by also considering HPV DNA and mRNA status.

Example 2

LSIL-HPV

Materials and Methods

Sample Collection

This current study was approved by the Research Ethics Committee at the Coombe Women and Infants University Hospital (CWIUH), Dublin. A total of 39 cervical liquid based cytology samples (15 true negative (TN) specimens, 12 LSIL specimens and 12 HSIL specimens) were collected for this Raman study. True negative cytology samples were obtained from the cytology laboratory, CWIUH, Dublin, Ireland. The LSIL and HSIL cytology specimens were collected from the Colposcopy clinic, CWIUH, Dublin, Ireland. The collected smears were processed via ThinPrep® method. For ThinPrep®, an adequate sampling of cells was collected from the ectocervix of true negative, LSIL and HSIL patients using the cytobrush. The cytobrush was rinsed in the vial containing PreservCyt transport medium (Thin-Prep® Pap Test; Cytyc Corporation, Boxborough, Mass.). The vial was named with the patient name and ID and then sent to the cytology laboratory equipped with a ThinPrep® 2000 processor (Hologic Inc., Marlborough, Mass. 01752). The ThinPrep® Pap test filter rotates within the sample vial and produces mild current that separates the debris and mucus without affecting the appearance of the cells. A gentle vacuum collects the cells on the exterior surface of the Pap test filter membrane. The filter is then inverted and gently pressed against the glass ThinPrep® slide. A gentle air pressure and surface tension helps the cells to adhere to the slide and creates an evenly distributed monolayer deposit of cells with a diameter of ~20 mm. The slide was then transferred into a fixative bath of 95% ethanol automatically. The slide was then air dried and then the Raman spectral measurements were performed.

All samples were tested for HPV DNA status using the Cobas HPV DNA test (Roche) and LSIL and HSIL samples were further tested for HPV mRNA status using the APTIMA HPV mRNA test (Hologic).

Instrumentation

Cell Raman spectra were acquired using a HORIBA Jobin Yvon XploRA® system (Villeneuve d'Ascq, France). The Raman microscopy system combines an Olympus microscope BX41 equipped with a ×100 objective (MPlanN, Olympus, NA=0.9). The spectroscopy system incorporates a 532-nm diode laser, 1200 lines/mm grating and an air-cooled CCD detector (Andor, 1024×256 pixels). Silicon (spectral peak at 520.7 $cm^{-1}$) was used as the reference standard for the wavelength calibration. Intensity correction was performed using a relative intensity correction standard (NIST 2242). Each Raman spectrum from the cells was recorded with the laser power of ~1 mW on the sample, with an integration time of 30 sec and 2 accumulations. Following the Raman measurement on each cell, the image of the cell along with its x- and y-coordinates was also obtained.

A total of 548 Raman spectra (true negative=167, LSIL=204 and HSIL=177) were collected from the recruited 39 patients. Out of 204 spectra from LSIL cases, 66 spectra were HPV Cobas-negative (HPV DNA-negative), HPV Aptima-negative (HPV mRNA-negative) (CNAN); 69 were HPV Cobas-positive (HPV DNA-positive) and Aptima-negative (HPV mRNA-negative) (CPAN); 69 spectra were HPV Cobas-positive (HPV DNA-positive) and Aptima-positive (HPV mRNA-positive) (CPAP).

Data Analysis

All the recorded Raman spectra from true negative, LSIL and HSIL categories were subjected to data pretreatment including glass background correction, baseline correction and normalization. Following the data pretreatment, the Raman spectra were then mean centered to remove any magnitude dependency. The multi-class partial least squares discriminant analysis (PLS-DA) together with leave-one patient-out cross-validation model was developed for the mean-centered spectral dataset. The multivariate PLS-DA analysis was performed using the PLS toolbox (Eigenvector Research, Wenatchee, Wash.) in the Matlab® (Mathworks Inc., Natick, Mass.) scripting environment.

Results

Figure 8A:
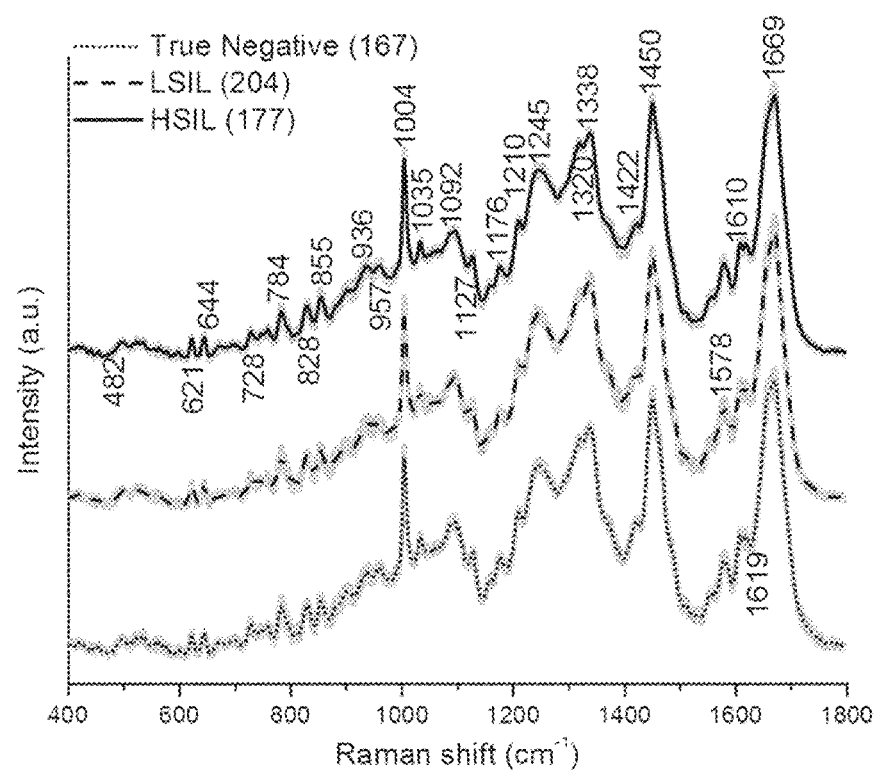
FIG. 8(a) Mean Raman spectra±1 standard deviation (SD) acquired from the negative, low-grade squamous intraepithelial lesion (LSIL) and high-grade squamous intraepithelial lesion (HSIL) ThinPrep® specimens (n=39) collected during routine Pap smear, (b) Difference Raman spectra±1 standard deviation (SD) of (a) negative–low-grade squamous intraepithelial lesion (LSIL) (b) negative–high-grade squamous intraepithelial lesion (HSIL)
Figure 8B:
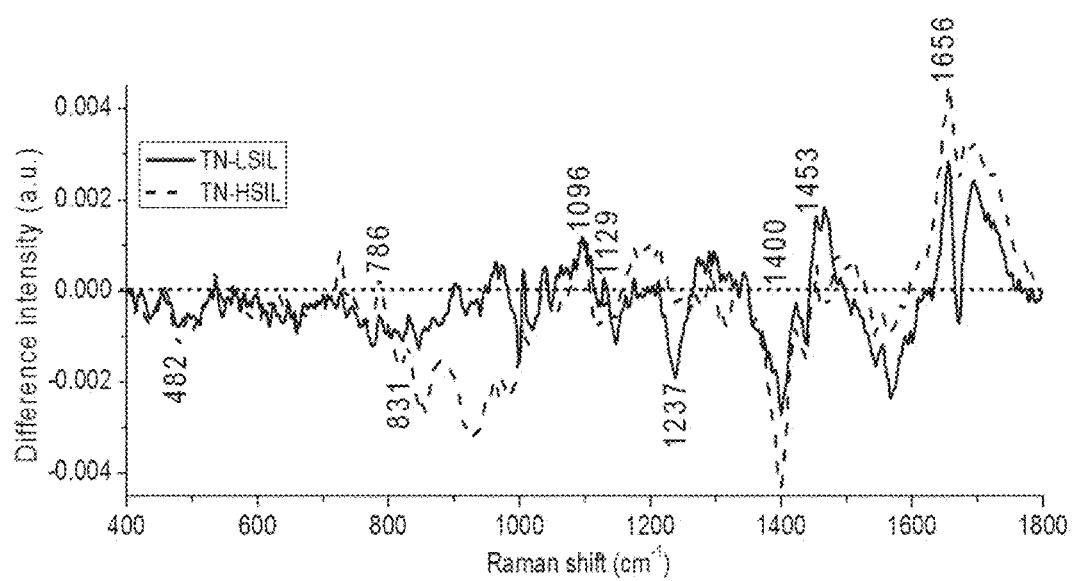

A total number of 548 Raman spectra were acquired from the true negative specimens (n=167) and from the morphologically normal appearing cells from LSIL (n=204) and HSIL (n=177) specimens (FIG. 8a). The acquired Raman spectrum shows peaks at 482 $cm^{-1}$ (glycogen), 621 and 644 $cm^{-1}$ (proteins), 728 and 784 $cm^{-1}$ (DNA), and 828 $cm^{-1}$ (DNA/RNA), 855 and 936 $cm^{-1}$ (glycogen and proteins), 957 $cm^{-1}$ (DNA), 1004 $cm^{-1}$ (phenylalanine), 1035 $cm^{-1}$ (proteins), 1092 $cm^{-1}$ (DNA phosphate backbone), 1127 $cm^{-1}$ (proteins), 1176 $cm^{-1}$ (cytosine/guanine), 1210 $cm^{-1}$ (tryptophan and phenylalanine), 1245 $cm^{-1}$ (amide III), 1320 $cm^{-1}$ (DNA/RNA, proteins, amide III), 1338 $cm^{-1}$ (proteins and nucleic acids), 1422 $cm^{-1}$ (related to the DNA/RNA content), 1450 $cm^{-1}$ (proteins, lipids), 1578 $cm^{-1}$ (nucleic acids), 1610 $cm^{-1}$ (phenylalanine, tyrosine), 1619 $cm^{-1}$ (heme), and 1669 $cm^{-1}$ (amide I). The difference spectra (FIG. 8b) show changes around 482, 786, 831, 1096, 1129, 1237, 1400, 1453 and 1656 $cm^{-1}$. In general, the protein band is stronger (1669 $cm^{-1}$) in negative samples and DNA and nucleic acids (1422 and 1578 cm$^{-1}$) are stronger in the abnormal samples.

Figure 9A:
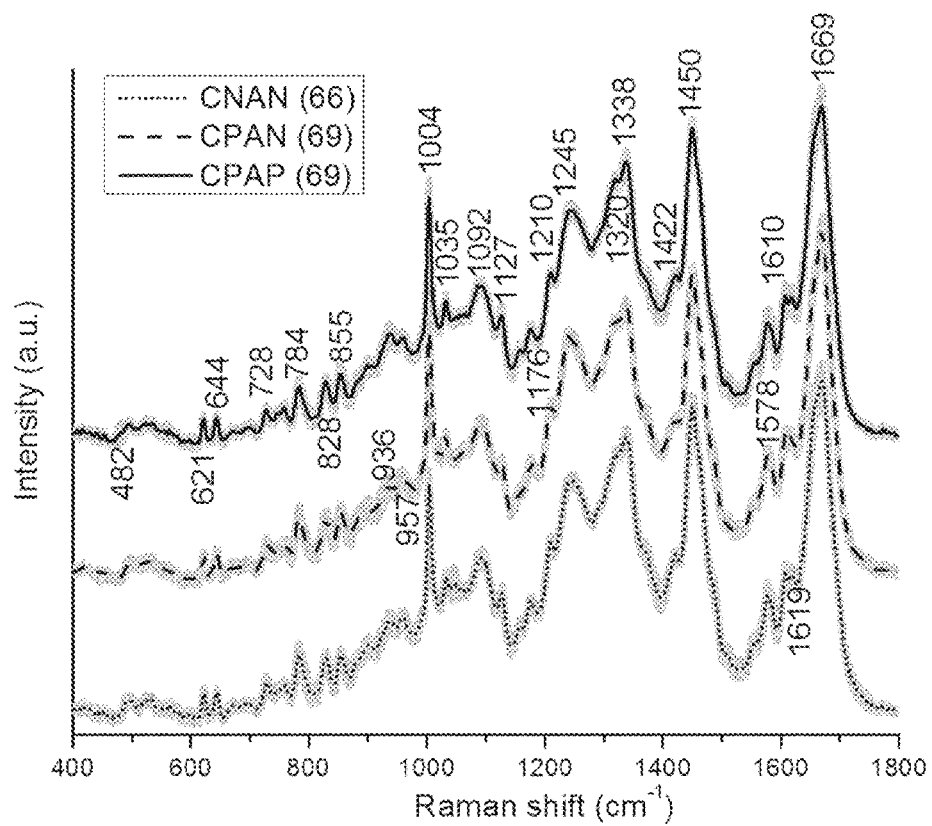
FIG. 9(a) Mean Raman spectra±1 standard deviation (SD) acquired from the low-grade squamous intraepithelial lesion (LSIL) ThinPrep® specimens (n=12) with different HPV test results (a) Cobas-negative and Aptima-negative, (b) Cobas-positive and Aptima-negative, (c) Cobas-positive and Aptima-positive; (b) Difference Raman spectra±1 standard deviation (SD) calculated from LSIL ThinPrep® specimens with different HPV test results (a) Cobas-negative Aptima-negative–Cobas-positive Aptima-negative (b) Cobas-negative Aptima-negative–Cobas-positive Aptima-positive (c) Cobas-positive Aptima-negative–Cobas-positive Aptima-positive.
Figure 9B:
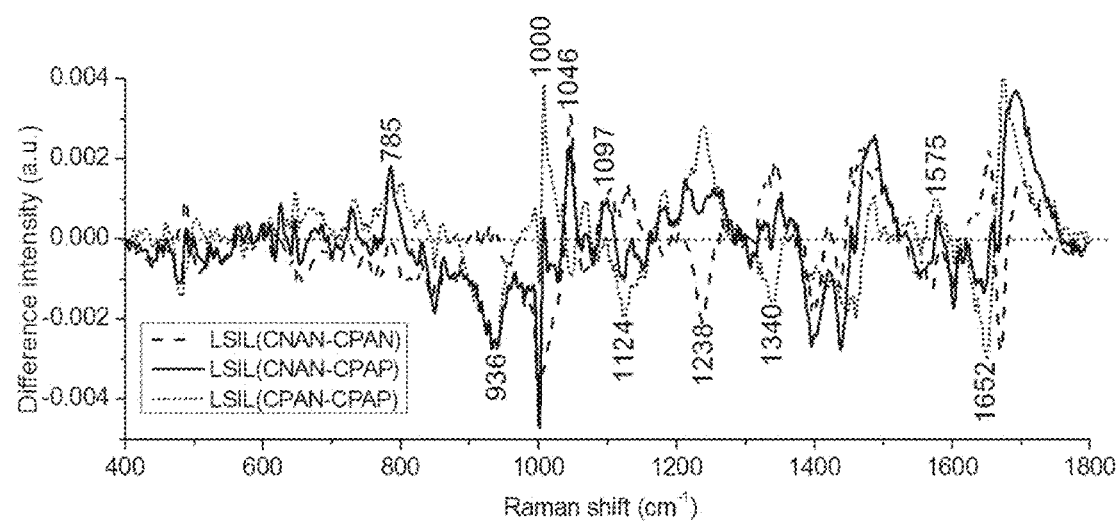

The Cobas HPV DNA and Aptima HPV mRNA assays were used to categorize the LSIL samples based on HPV result. There are three categories according to HPV result (i.e., CNAN, CPAN, and CPAP) and the corresponding mean spectrum for each category is shown in FIG. 9a. The difference spectra among different categories of LSIL are also shown in FIG. 9b, depicting the important differences around the Raman peaks 785, 936, 1000, 1046, 1097, 1124, 1238, 1340, 1575 and 1652 cm$^{-1}$. For instance, 1652, 1340, 1046 cm$^{-1}$ are higher in LSIL-CNAN.

Figure 10:
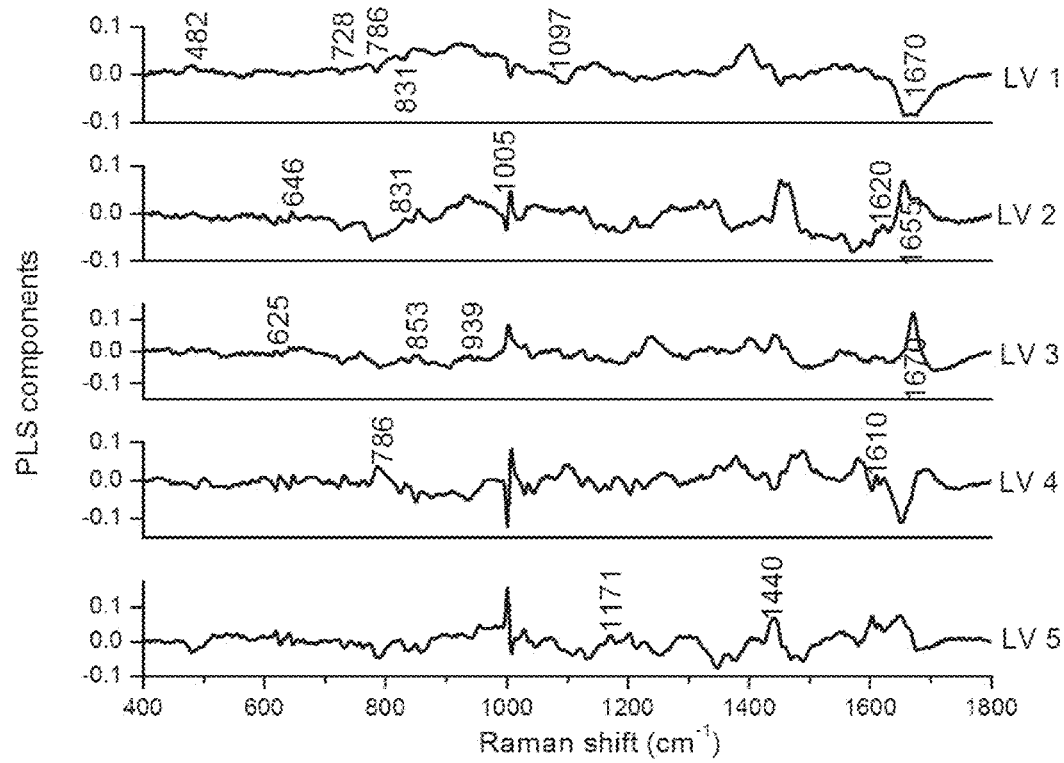
FIG. 10 PLS loadings (LVs) of the multi-class PLS-DA model developed from the dataset of true negative, low-grade squamous intraepithelial lesion (LSIL) and high-grade squamous intraepithelial lesion (HSIL) cytology specimens. (Latent variables (LVs), partial least squares discriminant analysis (PLS-DA))
Figure 11:
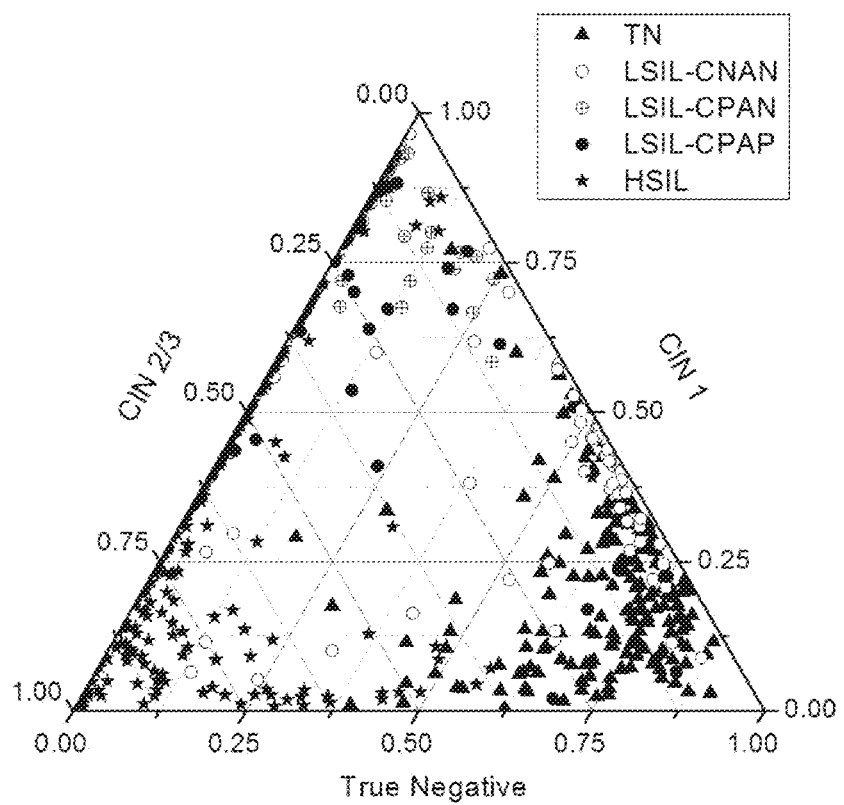
FIG. 11 Scatter plot of the posterior probability values obtained from the dataset of true negative, low-grade squamous intraepithelial lesion (LSIL) and high-grade squamous intraepithelial lesion (HSIL) cytology specimens.

As these differences among the spectra measured from true negative, LSIL and HSIL are very subtle, chemometrics including PLS-DA model was utilized to discern the minor differences among true negative, LSIL and HSIL. The multi-class PLS-DA model together with leave-one patient-out, cross-validation was developed using 5 PLS components corresponding to the minimum cross-validation error. The model was built and categorized into true negative, LSIL and HSIL based on the gold standard histology result, negative, CIN1 or CIN2/3. The total variance explained by the PLS components (latent variables (LVs)) are 59.76% in X-direction (LV1-23.31%, LV2-14.95%, LV3-6.45%, LV4-8.03%, LV5-7.01%) and 61.56% in Y-direction (LV1-21.02%, LV2-14.52%, LV3-15.43%, LV4-5.80%, LV5-4.80%). The PLS components extracted the information around the major Raman peaks (482, 625, 646, 728, 786, 831, 853, 939, 1005, 1097, 1171, 1440, 1610, 1620, 1655 and 1670 cm$^{-1}$), related to the changes in cell biochemical constituents such as glycogen, nucleic acids, heme, proteins, and lipids associated with different grades of cervical pre-cancer (FIG. 10). The posterior probability for each sample was calculated from the PLS scores. The posterior probability plot provided sensitivity of 89.2%, 63.2% and 81.4% and specificity of 85.3%, 89.0% and 91.4% for identifying true negative, LSIL and HSIL (Table 3). The posterior probability plot (FIG. 11) shows that the true negative and HSIL samples can be separated very well, but different categories in the LSIL samples are clustered differently. Out of 204 LSIL spectra, 66 spectra belong to LSIL-CNAN, 69 spectra to LSIL-CPAN and 69 spectra to LSIL-CPAP. Among 66 spectra from LSIL-CNAN, 43 are classified as true negative, 14 as LSIL and 9 as HSIL. Most of the LSIL-CNAN samples are misclassified as true negative because of their similarity to the true negative samples. This is most likely because there is no HPV presence/integration in the host cell. Out of 69 LSIL-CPAN samples, 68 of them classified as LSIL indicating that they are distinct from true negative or HSIL cases. Out of 69 LSIL-CPAP samples, 47 are classed as LSIL, 7 are classed as true negative and 15 are classified as HSIL. Many LSIL-CPAP samples are dispersed from CIN 1 towards CIN2/3, but not towards negative. This demonstrates that the patients with LSIL-CPAP may have a high risk of progression due to overexpression of the E6/E7 oncoproteins in the host cells i.e. the HPV genome is integrated with the host genome.

Thus, the Applicant has surprisingly found that high quality Raman spectra can be successfully acquired from morphologically normal appearing cells from true negative, LSIL and HSIL Thinprep® specimens and different grades of cervical pre-cancer can be separated with good sensitivities and specificities. Raman spectroscopy can further identify different categories of the LSIL cases i.e., whether they are likely to regress to negative or progress to HSIL cytology. This is an important finding and explains the mixed discrimination of LSIL cases. The presence of HPV E6/E7 mRNA indicates an active transforming HPV infection suggesting that these LSIL cases are more likely to progress to HSIL. Thus, the present invention provides a system and method of using Raman spectroscopy for discriminating between LSIL cases likely to progress to HSIL or cancer from those likely to regress. This represents an important unmet clinical need as a high proportion of women with LSIL who are at a relatively low risk of developing cancer undergo unnecessary colposcopy follow up and in many instances also undergo unnecessary treatment. A reliable test to identify LSIL cases likely to progress or regress would greatly improve management of women presenting with low grade cytological abnormalities.

Figure 12:
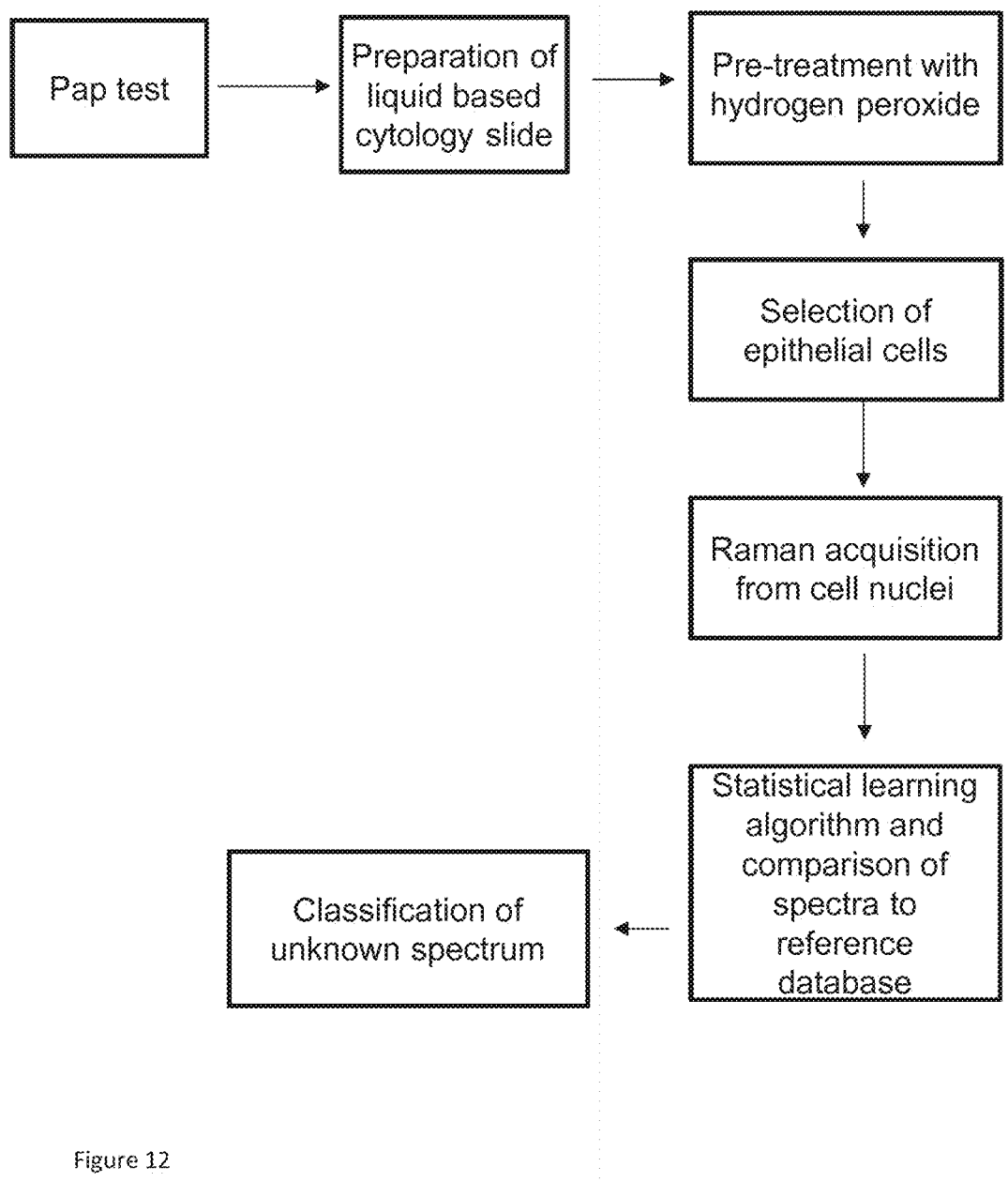
FIG. 12 is a schematic of a flow chart showing the steps involved in the method of the present invention.

Referring now to FIG. 12, the schematic flow chart shows the steps involved in carrying out the method of the present invention and the method will now be summarised with reference to FIG. 12.

The method of the present invention comprises the following steps:

1. Carrying out Pap test—cervical cells collected from the cervix using a cyto brush and rinsed in the specimen vial containing liquid preservative (ThinPrep® Pap Test or Sure-Path® Pap Test);

2. Preparation of liquid based cytology slide—Samples are prepared using Thin Prep® or SurePath® liquid based cytology method—cells are transferred onto a glass slide to create a monolayer of cells;

3. Pre-treatment with hydrogen peroxide—before Raman measurement, each slide is pre-treated with hydrogen peroxidase ($H_2O_2$) to remove any contaminating blood and debris;

4. Selection of epithelial cells—slide placed on the Raman microscope, and using low power objective lens (eg. ×10 or ×20), unstained cervical epithelial cells (intermediate and superficial cells) visualized as polygonal cells with small nuclei and large cytoplasm;

5. Raman acquisition from cell nuclei—using high power objective lens (×100), laser (532 nm) directed at cell nuclei and Raman spectra acquired (eg. integration time of 30 sec and 2 accumulations); and 6. Carry out statistical learning algorithm and comparison of spectra to reference database/Classification of unknown spectrum—Raman spectra pre-processed by correcting for glass background using least-squares method with non-negative constraints (NNLS) method and for baseline. Vector normalisation and mean centring carried out. Unknown spectra tested against the classification model.

The above referenced pre-treatment step (step 3 above) with hydrogen peroxide is described in detail in the Applicant's patent specification No. EP2984488.

REFERENCES

1. Kitchener H. C.; Blanks R.; Cubie H.; Desai M.; Dunn G.; Legood R.; Gray A.; Sadique Z.; Moss S. (2011) MAVARIC Trial Study Group. MAVARIC—A comparison of automation-assisted and manual cervical screening: A randomised controlled trial. Health Technol. Assess., 15:1-170.
2. Ellis, D. I.; Cowcher, D. P.; Ashton, L.; O'Hagan, S.; Goodacre, R. Illuminating disease and enlightening biomedicine: Raman spectroscopy as a diagnostic tool. Analyst 2013, 138, 3871-3884.
3. Kendall, C.; Isabelle, M.; Bazant-Hegemark, F.; Hutchings, J.; Orr, L.; Babrah, J.; Baker, R.; Stone, N. (2009) Vibrational spectroscopy: A clinical tool for cancer diagnostics. Analyst, 134:1029-1045.

4. Nijssen, A.; Koljenovic, S.; Bakker Schut, T. C.; Caspers, P. J.; Puppels, G. J. (2009) Towards oncological application of Raman spectroscopy. J. Biophotonics, 2:29-36.
5. Jess P. R. T., Simth D. D. W., Mazilu M., Dholakia K., Riches A. C., Herrington C. S. (2007) Early detection of cervical neoplasia by Raman spectroscopy. International Journal of Cancer 121:2723-2728.
6. Ostroswka K. M., Malkin A., Meade A., O'Leary J., Martin C., Spillane C., Byrne H. J., Lyng F. M. (2010) Investigation of the influence of high-risk human papillomavirus on the biochemical composition of cervical cancer cells using vibrational spectroscopy. Analyst 135: 3087-3093.
7. Vargis, E.; Tang, Y.-W.; Khabele, D.; Mahadevan-Jansen, A. (2012) Near-infrared Raman Microspectroscopy Detects High-risk Human Papillomaviruses. Transl. Oncol. 5: 172-179.
8. Kelly J G, Cheung K T, Martin C, O'Leary J J, Prendiville W, Martin-Hirsch P L, Martin F L. A spectral phenotype of oncogenic human papillomavirus-infected exfoliative cervical cytology distinguishes women based on age. Clin Chim Acta. 2010 Aug. 5; 411(15-16):1027-33.
9. Schubert J M, Bird B, Papamarkakis K, Miljković M, Bedrossian K, Laver N, Diem M. Spectral cytopathology of cervical samples: detecting cellular abnormalities in cytologically normal cells. Lab Invest. 2010 July; 90(7): 1068-77.

REFERENCES I-V

[i] Rana D N, Marshall J, Desai M, Kitchener H C, Perera D M, El Teraifi H, Persad R V. Five-year follow-up of women with borderline and mildly dyskaryotic cervical smears. Cytopathology. 2004 15(5):263-70.
[ii] Melnikow J, Nuovo J, Willan A R, Chan B K, Howell L P. Natural history of cervical squamous intraepithelial lesions: a meta-analysis. Obstet Gynecol. 1998 92(4 Pt 2):727-35
[iii] Bentley E, Cotton S C, Cruickshank M E, Duncan I, Gray N M, Jenkins D, Little J, Neal K, Philips Z, Russell I, Seth R, Sharp L, Waugh N; Trial of Management of Borderline and Other Low-Grade Abnormal Smears (TOMBOLA) Group. Refining the management of low-grade cervical abnormalities in the UK National Health Service and defining the potential for human papillomavirus testing: a commentary on emerging evidence. J Low Genit Tract Dis. 2006 10(1):26-38.
[iv] Cox J T; American Society for Colposcopy and Cervical Pathology. The clinician's view: role of human papillomavirus testing in the American Society for Colposcopy and Cervical Pathology Guidelines for the management of abnormal cervical cytology and cervical cancer precursors. Arch Pathol Lab Med. 2003 127(8):950-8.
[v] Bosch F X, Manos M M, Muñoz N, et al. Prevalence of human papillomavirus in cervical cancer: a worldwide perspective. International biological study on cervical cancer (IBSCC) study group. Journal of the National Cancer Institute 87(11):796-802 (1995)

Clauses

1. A cytology system for analyzing a biological sample on a glass slide, the system comprising: a stage for receiving the sample holder, a low resolution Raman spectroscopy device having a spectral resolution worse than 3 wavenumbers, the Raman spectroscopy device having an analysis module for determining whether the spectrum falls within one or more predefined classes of cell.

2. A system according to clause 1, wherein the biological sample is a Pap smear on a glass slide.

3. A system according to clause 1 or clause 2, wherein the one or more predefined classes comprise the following: a) normal b) invasive carcinoma and c) cervical intraepithelial neoplasia (CIN).

4. A system according to clause 3, wherein the one or more predefined classes are further delineated into one of the classifications of low-grade squamous intraepithelial lesions (LSIL) and high-grade squamous intraepithelial lesions (HSIL) and optionally, may be delineated into the classes of: a) LSIL (CIN I); and HSIL which comprises b) CIN II and C) CIN III.

5. A system according to any preceding clause, wherein the image analysis identifies cells as areas of interest.

6. A system according to any preceding clause, further comprising: a controller, and a microscope for viewing the sample holder, the microscope having a central optical axis, wherein the Raman spectroscopy device shares the central optical axis of the microscope, and wherein the controller is adapted to cause the stage to move an identified area of interest on the slide to be in-line with the central optical axis and to cause a spectrum to be obtained by the Raman spectroscopy device for the area of interest.

7. A system according to clause 6, further comprising a graphical user interface comprising a window display the view from the microscope, wherein the interface is configured to allow a user to use a pointer to identify the area of interest.

8. A system according to clause 7 wherein the result of the determination of whether the spectrum falls within one or more predefined classes of cell is displayed within the graphical user interface.

9. A system according to any one of clauses 6 to 8, wherein the analysis module is configured to perform image analysis on an image acquired by the microscope to identify areas of interest.

10. A system according to any one of clauses 6 to 9, wherein the system further comprises a light source for illuminating the slide, wherein the controller is adapted to switch off the light source when operating the Raman spectroscopy device.

11. A system according to any one of clauses 6 to 10 further comprising a moveable mirror for switching the optical path between the microscope and the Raman spectroscopy device, wherein the moveable mirror is responsive to the controller.

12. A method of analyzing biological samples where the biological sample is a Pap smear, the method comprising the steps of:
performing low resolution Raman sprectroscopy with a spectral resolution worse than 3 wavenumbers to obtain a spectrum for the biological sample, and analysing the spectrum to determine whether the spectrum falls within one or more predefined classes of cells.

13. A method according to clause 12, wherein the one or more predefined classes comprise the following: low-grade squamous intraepithelial lesions (LSIL) and high-grade squamous intraepithelial lesions (HSIL) and optionally, may be delineated into the classes of: a) LSIL (CIN I); and HSIL which comprises b) CIN II and C) CIN III.

14. A method according to clause 13, wherein the CIN class is further delineated into the classes of: a) CIN I b) CIN II and C) CIN III.

15. A method according to any one of clauses 12 to 14 wherein the method comprises using Raman Spectroscopy for identification of low-grade squamous intraepithelial lesions (LSIL) that are likely to progress to high-grade squamous intraepithelial lesions (HSIL).

16. A method according to any one of clauses 12 to 15 wherein superficial or classification method multivariate analysisintermediate epithelial cells are used in the method for discrimination of negative and low-grade squamous intraepithelial lesions (LSIL) and high-grade squamous intraepithelial lesions (HSIL) cytology cases.

17. A method according to any one of clauses 12 to 16 wherein the method comprises the step of sub classification of low-grade squamous intraepithelial lesions (LSIL) based on HPV status.

18. The method of the present invention comprises the following steps: Carrying out a Pap smear;
Preparation of liquid based cytology slide whereby cells are transferred onto a glass slide to create a monolayer of cells;
Pre-treatment using hydrogen peroxide to remove blood contamination; Selection of epithelial cells;
Acquiring Raman spectra from cell nuclei; and
Carrying out Statistical learning algorithm and comparison of spectra to reference database for Classification of unknown spectrum.

19. A method according to clause 18 wherein the step of selection of epithelial cells comprises placing the glass slide on the Raman microscope, and using low power objective lens unstained cervical epithelial cells (intermediate and superficial cells) visualized as cells with small nuclei and large cytoplasm.

20. A method according to clause 19 wherein the low power objective lens is of the order of ×10 or ×20 magnification.

21. A method according to clause 18 wherein the step of acquiring Raman spectra from cell nuclei comprises using a high power objective lens and laser directed at cell nuclei for acquiring the Raman spectra.

22. A method according to clause 21 wherein the laser is operated at approx. 532 nm and optionally, wherein the high power objective lens is of the order of ×100 magnification.

23. A method as per clause 18 wherein the step of carrying out statistical learning algorithm and comparison of spectra to reference database comprises Raman spectra pre-processing by correcting for glass background and for baseline and vector normalisation.

24. A method as per clause 23 wherein the step of correcting for glass background comprises using least-squares method with non-negative constraints (NNLS) method.

The invention claimed is:

1. A method for distinguishing between low-grade squamous intraepithelial lesions (LSIL) that are likely to progress to high-grade squamous intraepithelial lesions (HSIL) and LSIL that are likely to regress to negative, the method comprising:

providing a biological sample comprising cervical cells;
obtaining a Raman spectrum for the biological sample;
analysing the Raman spectrum to determine whether the Raman spectrum falls within one or more predefined classes of cells, wherein the one or more predefined classes of cells comprise cells comprising LSIL that are likely to progress to HSIL and cells comprising LSIL that are likely to regress to negative
wherein analysing the Raman spectrum to determine whether the Raman spectrum falls within one or more predefined classes of cells comprises using a classification model built using a database of reference Raman spectra.

2. The method as claimed in claim 1 wherein the classification model comprises multivariate statistical analysis.

3. The method as claimed in claim 2 wherein the multivariate statistical analysis is selected from the group consisting of Partial Least Squares Discriminant Analysis (PLS-DA), principal component analysis, linear discriminant analysis, support vector machines, and random forest.

4. The method as claimed in claim 1 wherein the biological sample is obtained during a Pap smear.

5. The method as claimed in claim 1 wherein the biological sample is processed using a liquid-based cytology test or conventional cytology.

6. The method as claimed in claim 1 wherein the biological sample comprises morphologically normal looking cells and the Raman spectrum is obtained for the morphologically normal looking cells.

7. The method as claimed in claim 1 wherein the biological sample comprises superficial and intermediate epithelial cells.

8. The method as claimed in claim 1 wherein the Raman spectrum is obtained from cell nuclei of the cells from the biological sample.

9. The method as claimed in claim 1 wherein the Raman spectrum is obtained using a low resolution Raman spectroscopy device.

10. The method as claimed in claim 1 wherein the step of analysing the Raman spectrum comprises analysing Raman peaks selected from one or more of the following: 482, 621, 728, 828, 855, 936, 957, 1092, 1176, 1210, 1338, 1422, 1450, 1578, 1610, 1619, 1669 cm$^{-1}$.

11. The method as claimed in claim 1 wherein the step of analysing the Raman spectrum comprises analysing Raman peaks selected from one or more of the following: 785, 936, 1000, 1046, 1097, 1124, 1238, 1340, 1575 and 1652 cm$^{-1}$.

12. The method as claimed in claim 1 wherein the method does not include a separate step of screening for the presence of HPV DNA and HPV mRNA.

* * * * *